(12) United States Patent
Niizeki

(10) Patent No.: US 8,422,628 B2
(45) Date of Patent: Apr. 16, 2013

(54) MEDICAL X-RAY CT IMAGING APPARATUS

(75) Inventor: Ryuichiro Niizeki, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 163 days.

(21) Appl. No.: 12/803,187

(22) Filed: Jun. 21, 2010

(65) Prior Publication Data

US 2010/0322377 A1    Dec. 23, 2010

(30) Foreign Application Priority Data

Jun. 22, 2009  (JP) ................................. 2009-147236

(51) Int. Cl.
*G01N 23/00* (2006.01)
(52) U.S. Cl.
USPC ................................. 378/20; 378/4
(58) Field of Classification Search ................. 378/4–20
See application file for complete search history.

(56) References Cited

U.S. PATENT DOCUMENTS

| 3,908,126 | A | 9/1975 | Hudson et al. |
| 7,388,941 | B2 | 6/2008 | Sukovic et al. |
| 2004/0258210 | A1 | 12/2004 | Ritter |
| 2006/0293582 | A1 | 12/2006 | Jensen |
| 2008/0137802 | A1 | 6/2008 | Suzuki et al. |
| 2008/0260095 | A1 | 10/2008 | Sukovic et al. |
| 2008/0273659 | A1* | 11/2008 | Guertin et al. ................... 378/65 |

FOREIGN PATENT DOCUMENTS

| DE | 43 00 740 C | 3/1994 |
| DE | 44 04 640 C | 2/1995 |
| DE | 101 46 915 A | 4/2003 |
| EP | 0 919 186 A | 6/1999 |
| JP | 2003-190132 A | 7/2003 |
| JP | 2007-330277 A | 12/2007 |
| WO | WO 03/045242 A | 6/2003 |
| WO | WO 2008/038283 A | 4/2008 |

* cited by examiner

*Primary Examiner* — Hoon Song
(74) *Attorney, Agent, or Firm* — DLA Piper LLP (US)

(57) ABSTRACT

Provided is a medical X-ray CT imaging apparatus including: a base (22); a support part (30) including a support arm part (30) that supports an X-ray source (36) and an X-ray detector (37) so as to be opposed to each other, and a rotation support part that supports the support arm part (32) in a rotatable manner with respect to the base (22); and a rotary drive part that rotatively drives the support part (30). At least one of the base (22) and the rotary support part (40) includes a cavity (48) forming a space around a rotation axis (A). The cavity (48) is provided with a cylindrical body (60) disposed in a rotatable state with respect to the support part (30).

22 Claims, 31 Drawing Sheets

F I G . 8
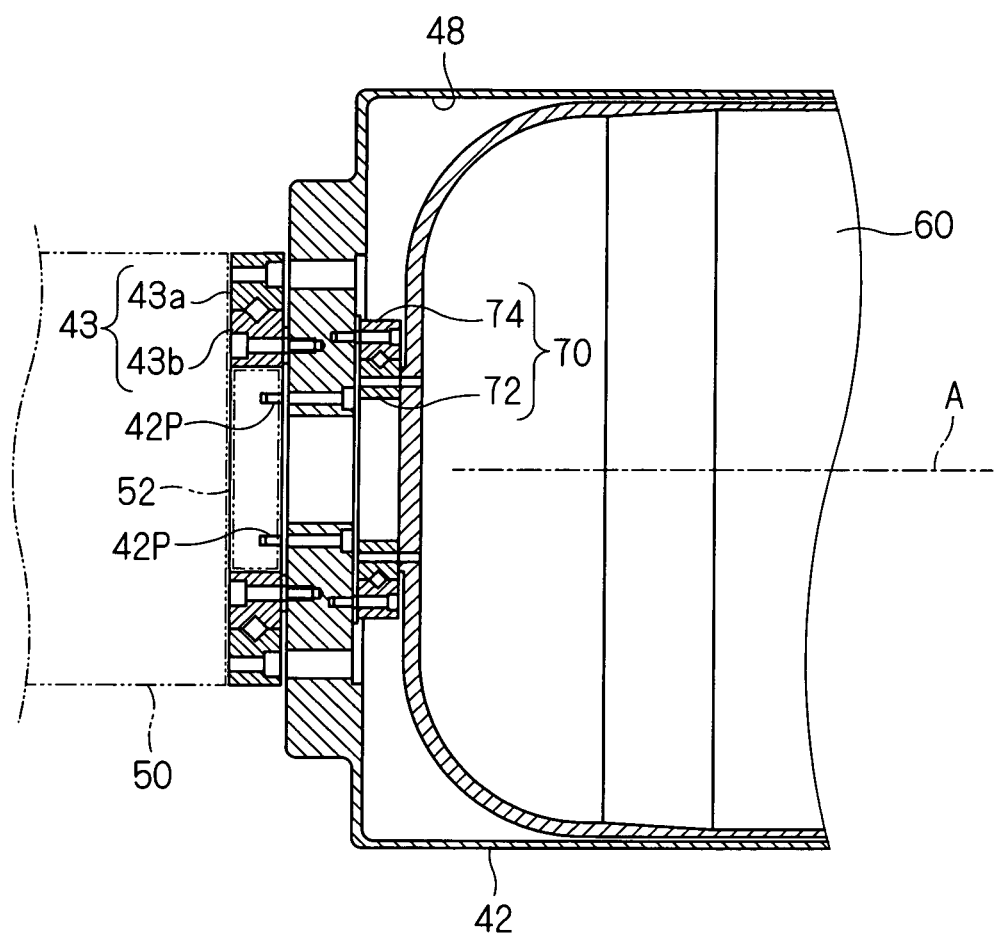

F I G . 9
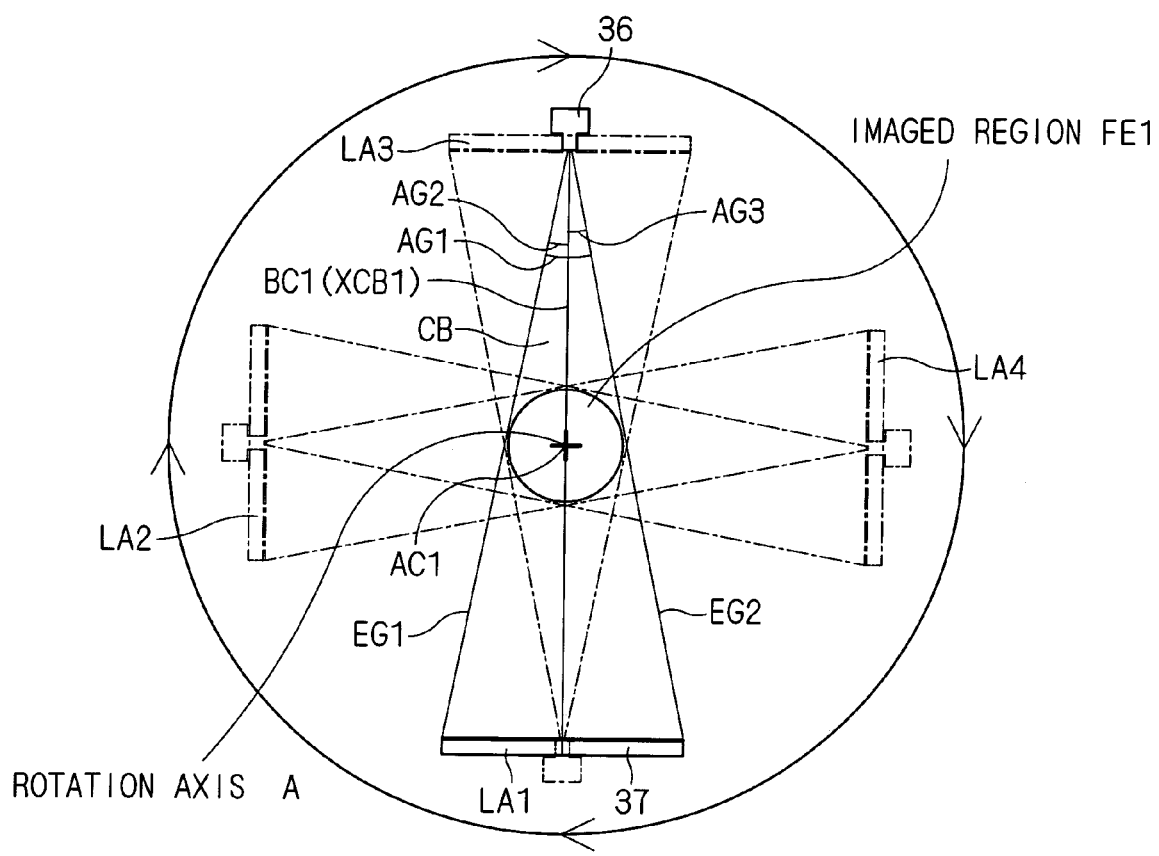

F I G . 1 0
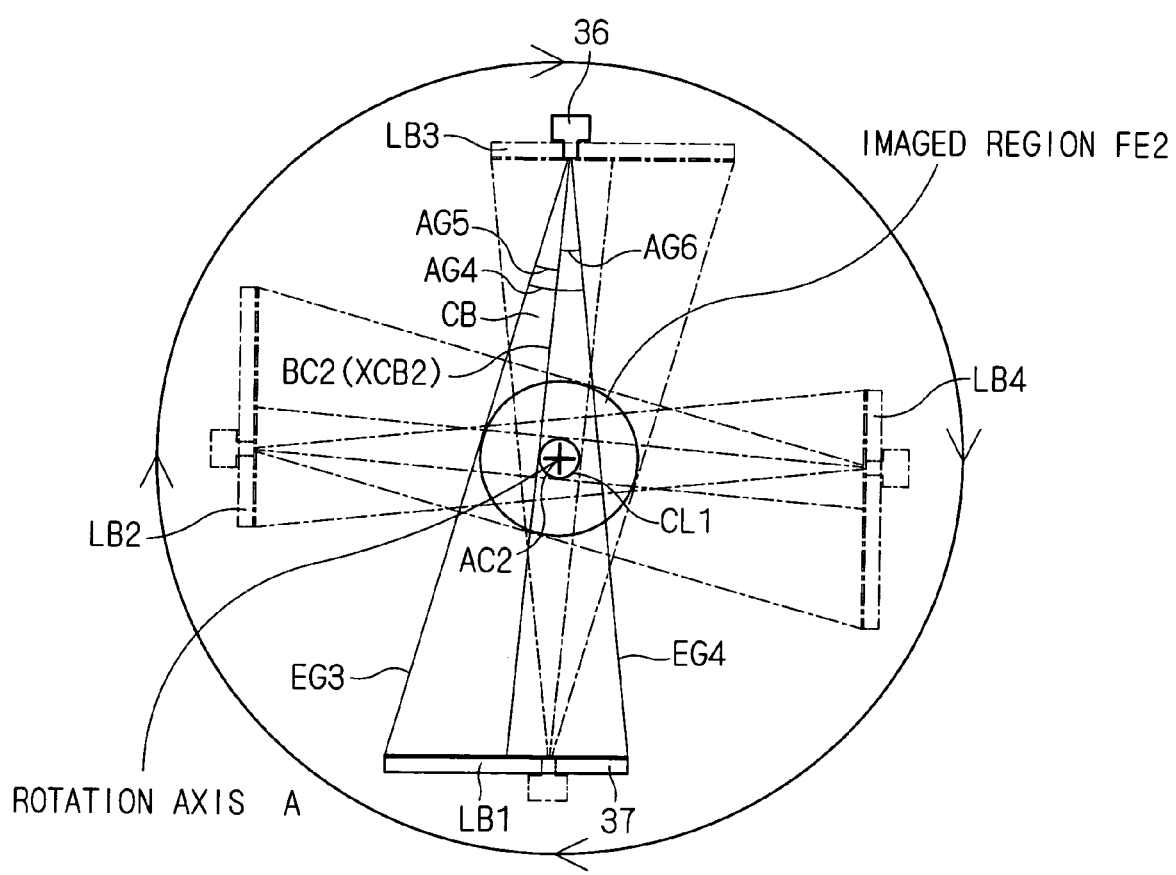

F I G . 1 3
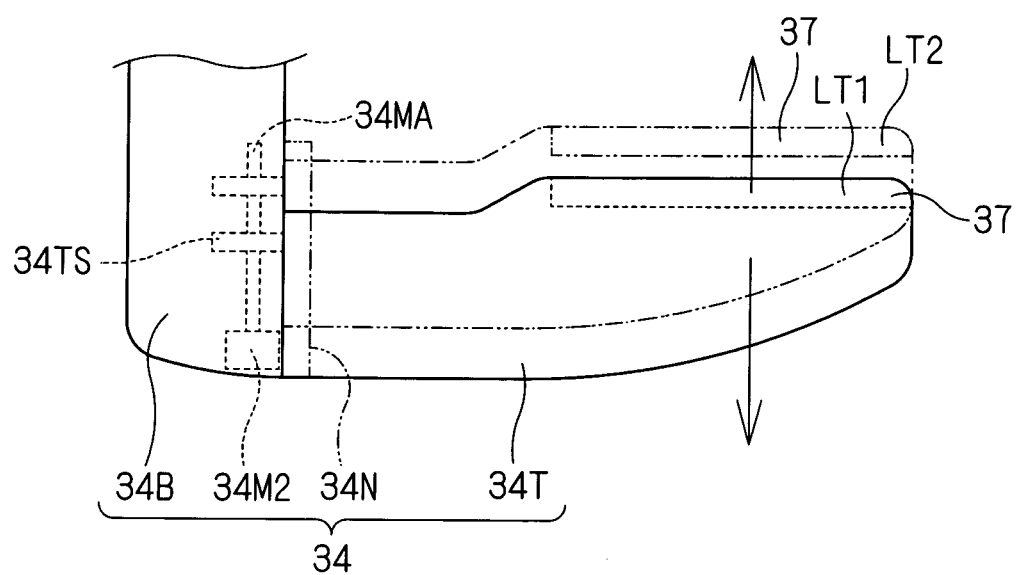

F I G. 3 2
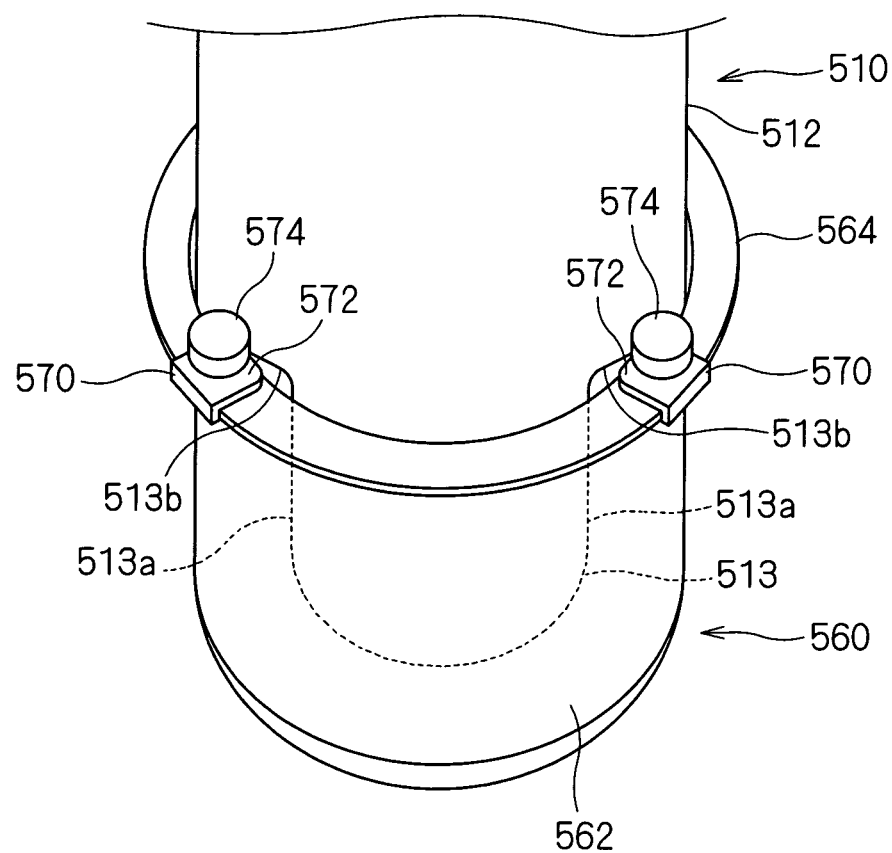

F I G . 4 0
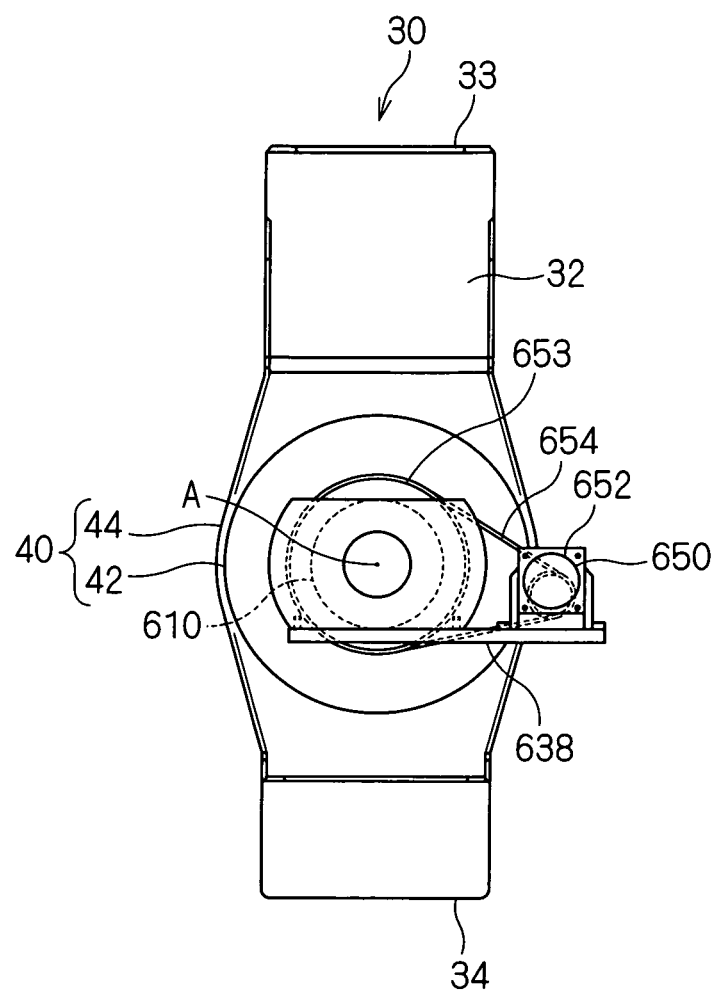

MEDICAL X-RAY CT IMAGING APPARATUS

BACKGROUND OF THE INVENTION

1. Field of the Invention

The present invention relates to an X-ray CT imaging apparatus used in medical diagnosis or the like, and more particularly, to an X-ray CT imaging apparatus that takes an image of a part of a patient such as a limb joint and a breast.

2. Description of the Background Art

Conventionally, as an X-ray CT imaging apparatus that takes an image of a part of a patient, there is one disclosed in US 2008/260095 A1.

US 2008/260095 A1 discloses the portable CT imaging apparatus that takes an image of a head of a patient. In the CT imaging apparatus, an X-ray source and an X-ray detector are supported by a first arm in a state of being arranged so as to be opposed to each other, and the first arm is supported so as to be rotatively driven by a motor. The first arm is rotated in a state where the head is disposed between the X-ray source and the X-ray detector, whereby the X-ray source and the X-ray detector are rotated around the head, to thereby perform X-ray CT imaging.

SUMMARY OF THE INVENTION

However, in the CT imaging apparatus disclosed in US 2008/260095 A1, a one side portion of a rotation axis of the first arm is configured to be occupied by a motor, a bearing structure and the like. For this reason, limitations are imposed on a mode in which an affected part is disposed with respect to the X-ray source and the X-ray detector. For example, the presence of the motor, the bearing structure and the like makes it difficult to dispose an upper arm, a hip joint, a chest or the like of a patient in the space between the X-ray source and the X-ray detector.

An object of the present invention is therefore to minimize limitations when a part of a patient is disposed between the X-ray source and the X-ray detector while keeping simplicity of the structure of the apparatus.

In order to solve the above-mentioned problem, a first aspect relates to a medical X-ray CT imaging apparatus performing CT imaging of a part of a patient, which includes: a base; a support part including a support arm part supporting an X-ray source generating an X-ray cone beam and an X-ray detector so as to be opposed to each other, and a rotation support part supporting the support arm part in a rotatable manner with respect to the base so that the X-ray source and the X-ray detector rotate about a rotation axis along a horizontal direction; and a rotary drive part rotatively driving the support part, wherein: at least one of the base and the rotation support part includes a cavity forming a space around the rotation axis; and the cavity is provided with a cylindrical body disposed in a rotatable state with respect to the support part, the cylindrical body being open to at least a space between the X-ray source and the X-ray detector.

According to the medical X-ray CT imaging apparatus of the first aspect, the spot to be imaged of a patient can be disposed between the X-ray source and the X-ray detector while disposing a portion in a vicinity of the spot to be imaged in the cavity. In addition, in this state, the support part is rotated to perform CT imaging while stopping the rotation of the cylindrical body. Accordingly, it is possible to minimize limitations when a part of a patient is disposed between the X-ray source and the X-ray detector.

According to a second aspect, in the medical X-ray CT imaging apparatus according to the first aspect, the cylindrical body is formed in a cylindrical shape with the rotation axis being a center axis, and is rotatably held by the rotation support part through a bearing.

According to the medical X-ray CT imaging apparatus of the second aspect, the cylindrical body is rotatably held by the rotation support part through the bearing, and hence fewer limitations are imposed on the layout of the rotary drive part that rotatively drives the support part.

According to a third aspect, in the medical X-ray CT imaging apparatus according to the first or second aspect, the cylindrical body is formed in a cylindrical shape with the rotation axis being a center, and is mounted onto the base.

According to the medical X-ray CT imaging apparatus of the third aspect, it is possible to prevent the cylindrical body from rotating during the rotation of the support part more reliably.

According to a fourth aspect, in the medical X-ray CT imaging apparatus according to the third aspect, the cylindrical body is mounted onto the base so as not to perform relative rotation around the rotation axis.

According to the medical X-ray CT imaging apparatus of the fourth aspect, it is possible to prevent the cylindrical body from rotating during the rotation of the support part more reliably.

According to a fifth aspect, in the medical X-ray CT imaging apparatus according to the third aspect, the cylindrical body is mounted onto the base in a rotationally adjustable manner around the rotation axis.

According to the medical X-ray CT imaging apparatus of the fifth aspect, it is possible to make adjustment in rotation of the cylindrical body in accordance with a state of a portion in the vicinity of the spot to be imaged that is disposed in the cylindrical body.

According to a sixth aspect, in any one of the first to fifth aspects, the medical X-ray CT imaging apparatus further includes a two-axially moving mechanism part enabling the support part to move along two axial directions, the two axial directions being orthogonal to the rotation axis and being orthogonal to each other.

According to the medical X-ray CT imaging apparatus of the sixth aspect, the support part is moved in the two axial directions, which makes it easy to adjust positions of the X-ray source and the X-ray detector with respect to the spot to be imaged. Accordingly, the patient is not required to move when a minute adjustment is made to the position, which alleviates a burden on the patient.

According to a seventh aspect, in any one of the first to sixth aspects, the medical X-ray CT imaging apparatus further includes a rotation axis direction moving mechanism part enabling the support part to move along the rotation axis direction.

According to the medical X-ray CT imaging apparatus of the seventh aspect, the support part is moved in the rotation axis direction, which makes it easy to adjust positions of the X-ray source and the X-ray detector with respect to the spot to be imaged. Accordingly, the patient is not required to move when a minute adjustment is made to the position, which alleviates a burden on the patient.

According to an eighth aspect, in any one of the first to fifth aspects, the medical X-ray CT imaging apparatus further includes: a Y direction moving mechanism part moving the support part in a Y direction along the rotation axis direction; a Z direction moving mechanism part moving the support part in a Z direction along a vertical direction; and an X direction moving mechanism part moving the support part in an X direction orthogonal to the Y direction and the Z direction, wherein the Z direction moving mechanism part moves the Y direction moving mechanism part and the X direction moving mechanism part in the Z direction.

According to the medical X-ray CT imaging apparatus of the eighth aspect, the Y direction moving mechanism part and the X direction moving mechanism part that extend in the horizontal direction can be arranged in the vicinity of the rotation axis, which reduces a size of a part in the vicinity of a bottom of the base. Accordingly, a medical X-ray CT imaging apparatus having a configuration suitable for transportation is achieved with more ease.

According to a ninth aspect, in the medical X-ray CT imaging apparatus according to any one of the first to eighth aspects, the cylindrical body includes a holding part provided for holding a spot to be imaged of the patient at a given position.

According to the medical X-ray CT imaging apparatus of the ninth aspect, the portion in the vicinity of the spot to be imaged is held by the holding part, and hence it is possible to perform CT imaging in the state where the spot to be imaged of the patient is caused to stand still at a more specific position.

According to a tenth aspect, in any one of the first to ninth aspects, the medical X-ray CT imaging apparatus further includes an X-ray regulating part regulating an irradiated region of the X-ray cone beam from the X-ray source, to thereby enable local CT imaging.

According to the medical X-ray CT imaging apparatus of the tenth aspect, it is possible to perform local X-ray CT imaging for a more limited region, which alleviates an exposure amount.

According to an eleventh aspect, in the medical X-ray CT imaging apparatus according to any one of the first to tenth aspects, at least one of the support part and the cylindrical body is provided with a positioning light irradiation part irradiating light for positioning.

According to the medical X-ray CT imaging apparatus of the eleventh aspect, the spot to be imaged can be positioned more accurately between the X-ray source and the X-ray detector, which increases the possibility that re-imaging due to inappropriate positioning may be avoided.

According to a twelfth aspect, in the medical X-ray CT imaging apparatus according to any one of the first to eleventh aspects, the cylindrical body is provided with a connecting and separating part enabling an external holding member to be connected thereto and separated therefrom, the external holding member provided for holding a spot to be imaged at a given position.

According to the medical X-ray CT imaging apparatus of the twelfth aspect, X-ray CT imaging can be performed in the state where a bed, a support for an arm, or the like is connected to the cylindrical body. Accordingly, X-ray CT imaging can be performed in the state where the spot to be imaged of the patient is caused to stand still at a more specific position.

According to a thirteenth aspect, in the medical X-ray CT imaging apparatus according to any one of the first to twelfth aspects, the cylindrical body is formed in a bottomed cylindrical shape.

According to the medical X-ray CT imaging apparatus of the thirteenth aspect, various mechanisms are incorporated in the side of the base that is outside the bottom of the cylindrical body, which simplifies the configuration with ease.

According to a fourteenth aspect, in the medical X-ray CT imaging apparatus according to any one of the first to thirteenth aspects, an opening of the cylindrical body is provided with an extension part extending to an inside of a turning locus of the X-ray source and the X-ray detector around the rotation axis, the opening being open toward the space between the X-ray source and the X-ray detector.

According to the medical X-ray CT imaging apparatus of the fourteenth aspect, the contact between the spot to be imaged and the X-ray source or the X-ray detector is suppressed.

According to a fifteenth aspect, in the medical X-ray CT imaging apparatus according to the fourteenth aspect, the extension part is attached to the opening so as to be connected thereto and separated therefrom.

According to the medical X-ray CT imaging apparatus of the fifteenth aspect, the extension part is attached to the opening so as to be connected thereto and separated therefrom, and thus the extension part can be attached thereto and detached therefrom in accordance with the spot to be imaged. Therefore, it is possible to perform X-ray CT imaging at a variety of spots.

According to a sixteenth aspect, in the medical X-ray CT imaging apparatus according to any one of the first to fifteenth aspects, the base includes a wheel capable of rolling on a floor.

According to the medical X-ray CT imaging apparatus of the sixteenth aspect, the medical X-ray CT imaging apparatus can be easily moved.

According to a seventeenth aspect, in the medical X-ray CT imaging apparatus according to any one of the first to sixteenth aspects, the X-ray source is disposed during rotation of the support part so that: when viewed from the rotation axis direction, a side portion on one side of an irradiated region of the X-ray cone beam inevitably passes through a periphery of an imaged region and a side portion on the other side thereof passes through an inner side than the periphery of the imaged region; and when viewed from the rotation axis direction, the X-ray cone beam irradiates a region of a half or more of an entire region of the imaged region that is less than the entire region of the imaged region; and the support part is configured so as to turn 360° or more.

According to the medical X-ray CT imaging apparatus of the seventeenth aspect, an imaged region can be magnified with a simple structure, which makes it possible to cover a small target area such as an arm joint to a large target area such as a portion in the vicinity of a lumbar spine for imaging. Therefore, it is possible to achieve a medical X-ray CT imaging apparatus capable of effectively using an X-ray detector.

According to an eighteenth aspect, in any one of the first to seventeenth aspects, the medical X-ray CT imaging apparatus further includes a magnification changing mechanism causing the X-ray detector to be relatively close to or apart from the X-ray source, to thereby change a magnification.

According to the medical X-ray CT imaging apparatus of the eighteenth aspect, an imaged region can be magnified with a simple structure, which makes it possible to cover a small target area such as an arm joint to a large target area such as a portion in the vicinity of a lumbar spine for imaging. Therefore, it is possible to achieve a medical X-ray CT imaging apparatus capable of effectively using an X-ray detector.

BRIEF DESCRIPTION OF THE DRAWINGS

FIG. 8 is a partially enlarged cross-sectional view of FIG. 7;

FIG. 9 schematically shows a state of normal CT imaging;

FIG. 10 schematically shows a state of offset CT imaging;

FIG. 13 is a view showing another example of changing an imaged region;

FIG. 32 is a perspective view showing the connecting and separating part and the medical bed according to the third modification of the first preferred embodiment, which is viewed from downward;

FIG. 40 is a rear view showing the support part and the rotary drive part of the medical X-ray CT imaging apparatus according to the second preferred embodiment;

DESCRIPTION OF THE PREFERRED EMBODIMENTS

First Preferred Embodiment

Figure 6:
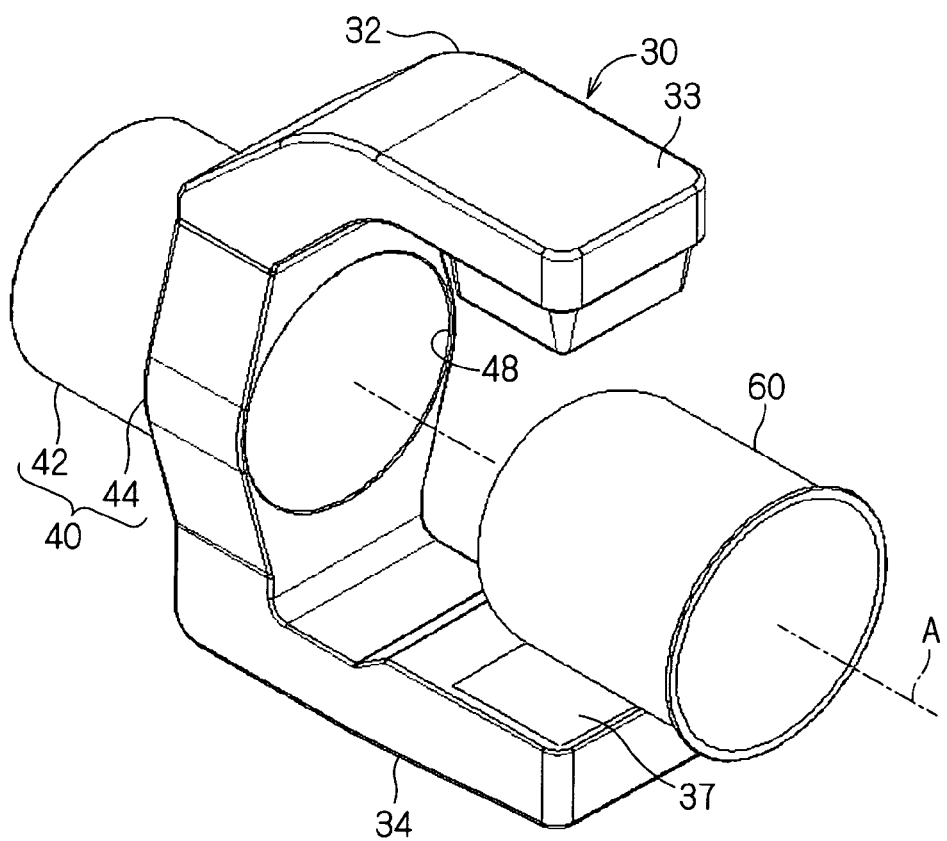
FIG. 6 is an exploded perspective view showing a support part and a cylindrical body of the medical X-ray CT imaging apparatus according to the first preferred embodiment.
Figure 7:
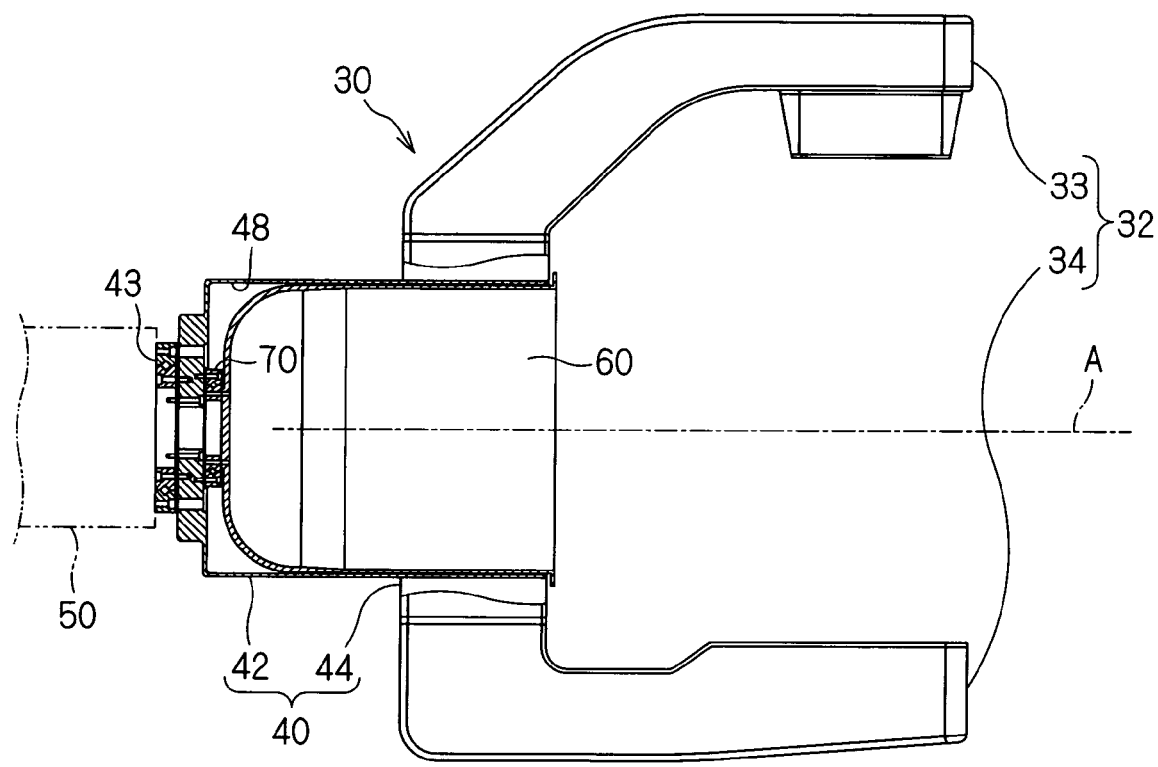
FIG. 7 is a cross-sectional view showing a rotation support part and the cylindrical body of the medical X-ray CT imaging apparatus according to the first preferred embodiment.

Hereinafter, description is given of a medical X-ray CT imaging apparatus according to a first preferred embodiment. FIGS. 1 to 5 are views showing a medical X-ray CT imaging apparatus 20 according this preferred embodiment, FIG. 6 is an exploded perspective view showing a support part 30 and a cylindrical body 60 of the medical X-ray CT imaging apparatus 20, and FIGS. 7 and 8 are cross-sectional views of main parts, which show a rotation support part 40 and the cylindrical body 60 of the medical X-ray CT imaging apparatus 20.

The medical X-ray CT imaging apparatus 20 is an apparatus for performing CT imaging of a part of a patient such as a head, cervical spine, arm joint, finger, breast, lumbar spine, hip joint, knee and leg, and includes a base 22, the support part 30, a rotary drive part 50 and the cylindrical body 60.

The base 22 is a portion serving as a base to which respective parts constituting the apparatus 20 are directly or indirectly assembled. The support part 30 and the cylindrical body 60 that are essential portions constituting the apparatus, which are described below, are provided to the base 22. In an example of views, the support part 30 and the cylindrical body 60 are provided on one principal surface of the base 22 along a vertical direction. Note that in the description below, for the sake of convenience, a side of the base 22 on which the support part 30 and the cylindrical body 60 are provided is referred to as a front side and a side opposite thereto is referred to as a rear side in some cases.

In addition, a lower part of the base 22 is provided with a pair of wheels 24 and an auxiliary wheel 25 that is capable of changing a direction as wheels capable of rolling on a floor. Further, a rear part of an upper side portion of the base 22 is provided with a manually operated handle 26. When a user or the like of the apparatus 20 holds the manually operated handle 26 to push the apparatus 20 while operating a traveling direction, the apparatus 20 runs and moves on the floor surface or the like, to thereby be conveyed to a desired position. That is, the medical X-ray CT imaging apparatus 20 is configured as a portable medical X-ray CT imaging apparatus 20 capable of changing its location. As described above, while the user or the like may hold the manually operated handle and push the apparatus 20 for conveyance, the wheels 24 may be driven by a driving mechanism using, for example, a motor (not shown).

Note that the configuration enabling the medical X-ray CT imaging apparatus 20 to move is not limited to the above-mentioned example. For example, the medical X-ray CT imaging apparatus 20 may be configured to include three or more wheels capable of changing a direction. Alternatively, the medical X-ray CT imaging apparatus 20 may be configured to include two wheels and a fixed leg and, when moving, move by rotation of two wheels in a state in which the fixed leg floats against the floor. At least one of the wheels may be provided with a brake for putting a brake on the rotation. Alternatively, at least one of the wheels may be provided with a known lock mechanism for performing rotational locking of the wheel, to thereby safely maintain a stop state of the medical X-ray CT imaging apparatus 20.

Further, the rear part of the upper side portion of the base 22 is provided with a display part 27 and an input part 28, and a CT imaging processing unit (not shown) is provided within the base 22. The display part 27 is a display device on which various information of CT imaging is displayed, such as a liquid crystal display device and an organic EL display device. The input part 28 is an input device that comprises multiple switches and the like for receiving various instructions of CT imaging. The input part 28 is only required to have a function of receiving an operation and, for example, various items such as a mouse, keyboard and touch pad are appropriately used. The display part 27 may comprise a touch pen and a display that receives an operation of the touch pen or may comprise a touch panel or a touch screen. In this case, the display part 27 also functions as the input part 28.

Further, the CT imaging processing unit is a processing control unit comprising, for example, a typical microcomputer including a CPU, ROM, RAM and the like. The CT imaging processing unit is configured to control the operation of the rotary drive part 50 during CT imaging and to perform, for example, the processing of reconstructing a CT image to be imaged based on an electrical signal obtained by an X-ray detector 37 through imaging, in accordance with various instructions input by software stored in advance, the input part 28 or the like. The taken CT image may be displayed on the display part 27 or on other display part through a wired or wireless communication line, or may be recorded in a recording medium such as a magnetic recording medium, an optical recording medium and a flash memory.

Further, a mounting hole part 20h is formed on one principal surface of the base 22, and the support part 30 and the cylindrical body 60 are provided to the base 22 with the use of the mounting hole part 20h.

The rotary drive part 50 comprises, for example, a motor capable of controlling a rotation speed, a rotation angle and the like. The rotary drive part 50 is supported at a given position in the base 22 or is supported so as to change its position in a position in which a drive axis part thereof is made to be substantially horizontal toward approximately a center of the mounting hole part 20h. Note that an example in which the rotary drive part 50 is supported in the base 22 so as to change its position is described below as a modification. The rotation support part 40, described below is connected to the rotary drive part 50, whereby the support part 30 is supported so as to be rotatively driven (see FIG. 8).

The support part 30 includes a support arm part 32 that supports an X-ray source 36 and the X-ray detector 37 in a state of being opposed to each other, and the rotation support part 40 that supports the support arm part 32 in a rotatable manner with respect to the base 22.

More specifically, the rotation support part 40 is configured by integrating an inner side rotation support part 42 and an outer side rotation support part 44. The inner side rotation support part 42 is formed in a bottomed cylindrical shape and is disposed in the base 22 through the mounting hole part 20h. The outer side rotation support part 44 is formed to become a member larger than the inner side rotation support part 42 (in this case, slightly larger) and is disposed in the mounting hole part 20h, at a position outside the base 22.

A bottom part of the inner side rotation support part 42 is provided with rotary drive bearing parts 43, in each of which an outer ring member 43a and an inner ring member 43b are connected in a relatively rotatable manner through, for example, a rolling element such as a ball. The rotary drive part 50 includes a casing that does not rotate and a rotator portion 52 that rotates with respect to the casing and projects from the casing. The outer ring members 43a are attached and fixed to the casing of the rotary drive part 50 through screws or the like, and the inner ring members 43b are attached and fixed to the bottom of the inner side rotation support part 42 through screws or the like. As a result, the rotation support part 40 is rotatably supported with respect to the casing that is an area to which the rotary drive part 50 is fixed (see FIG. 8). Further, on an outer surface of the bottom of the inner side rotation support part 42, multiple projections 42p are provided around a rotation axis A in a projecting manner, and the projections 42p are fitted into recessed parts of the rotator portion 52 on the rotary drive part 50 side (see FIG. 8). Then, a rotary driving force of the rotary drive part 50 is transmitted from the rotator portion 52 to the rotation support part 40, with the result that the rotation support part 40 is rotatively driven around the rotation axis A along a substantially horizontal direction. The bearing parts are provided as described above, which prevents a moment load generated by the support part 30 from being directly applied on the rotary drive part 50 even when the rotation axis A is substantially horizontal. Accordingly, it is possible to prevent the rotation axis from wobbling. Compared with the configuration in which the rotary drive bearing parts 43 are not provided and the inner side rotation support part 42 is directly fixed to the rotator portion 52, the moment load generated by the support part 30 can be dispersed more with the configuration described above.

Further, the support arm part 32 includes a pair of arm parts 33 and 34 that are supported in a cantilevered manner by the outer side rotation support part 44 with an interval therebetween. The pair or arm parts 33 and 34 and the outer side rotation support part 44 have an approximately U-shaped outer shape as a whole. The pair of arm parts 33 and 34 are supported so as to extend substantially in parallel with each other, and there is provided an interval between the pair of arm parts 33 and 34, in which a part of a patient to be imaged can be disposed. The support arm part 32 is supported by the rotation support part 40 so as to rotate and be rotatively driven around the rotation axis A with respect to the base 22.

The X-ray source 36 comprises an X-ray generator that generates an X-ray cone beam, such as an X-ray tube. The X-ray source 36 is mounted onto an inner surface side portion at a tip of the arm part 33 at a position and in a position where an X-ray cone beam can be irradiated toward a tip of the arm part 34. Note that an X-ray regulating part 36P that regulates an irradiated region of an X-ray cone beam is provided in front of the X-ray source 36 in an irradiation direction of X-rays therefrom. The X-ray regulating part 36P is a plate-like member in which an opening for regulating the spread of the X-ray cone beam is formed, and is referred to as a collimator in some cases. The opening is formed to have a slit shape or a substantially rectangular opening shape of a predetermined size, in accordance with a mode in which X-ray CT imaging is performed. As the plate-like member for forming the opening, various configurations are employed in accordance with a target region of CT imaging. For example, there may used the configuration in which one or multiple openings are provided to one plate, the configuration in which two or more plates are superimposed by being displaced from each other to form an opening, and the configuration in which two or more plates are disposed in a movable manner so as to change an opening shape and an opening area.

The X-ray detector 37 detects X-rays that have been irradiated from the X-ray source 36 and have passed through an affected part to be imaged, and comprises a flat panel detector (FPD) that has a two-dimensionally extending detection surface, an X-ray image intensifier (I. I) or the like. The X-ray detector 37 is mounted onto an inner surface side portion at the tip of the arm part 34 in a position in which X-rays from the X-ray source 36 are capable of being irradiated to the detection surface.

The X-ray source 36 and the X-ray detector 37 are configured to rotate around the rotation axis A when the rotation support part 40 and the support arm part 32 are rotated around the rotation axis A. With the above-mentioned configuration, it is possible to obtain multiple pieces of X-ray projection data obtained by imaging an affected part from multiple directions, which are required to reconstitute the CT image.

Note that the X-ray regulating part 36P and the X-ray detector 37 may be provided in a changeable manner in accordance with a mode in which X-ray CT imaging is performed (for example, a case where ranges in which X-ray CT imaging is performed differ).

Further, a positioning light irradiation part 38 that irradiates light for positioning is provided at the tip of the arm part 33. The positioning light irradiation part 38 comprises a light-emitting diode, electric lamp or the like and is configured to emit visible light. The positioning light irradiation part 38 is mounted onto the tip of the arm part 33 in a position where it is capable of irradiating light toward the space between the X-ray source 36 and the X-ray detector 37. The light irradiated from the positioning light irradiation part 38 is regulated by a shield in which a slit is formed, a lens or the like so as to indicate an imaged position by the X-ray source 36 and the X-ray detector 37. Here, as the mode in which the light irradiated form the positioning light irradiation part 38 indicates the imaged position, for example, there is conceivable a case where the light is irradiated aiming at the rotation axis A or a case where the light indicates a boundary of an imaged region. Alternatively, light may be irradiated linearly, or may be irradiated in a point-like or planar manner. Further, the position onto which the positioning light irradiation part 38 is mounted is not limited to the tip of the arm part 33, and the positioning light irradiation part 38 may be mounted onto, for example, other portion of the arm part 33, the arm part 34, the rotation support part 40 or the cylindrical body 60.

Formed in the rotation support part 40 is a cavity 48 that forms the space expanding around the rotation axis A. In this case, there is formed a cavity in a bottomed cylindrical shape that is open on the outer side rotation support part 44 and has a bottom on a back side of the inner side rotation support part 42 being in contact with the rotary drive part 50. In this preferred embodiment, the cavity 48 in a bottomed cylindrical shape is formed, which is open toward the outer surface of the outer side rotation support part 44, has the bottom on the back side of the inner side rotation support part 42, and has a center axis that substantially coincides with the rotation axis A. An outer periphery at an end on the opening side of the inner side rotation support part 42 in a bottomed cylindrical shape is fitted with and fixed to the cavity at the center of the outer side rotation support part 44. The cavity 48 preferably has an opening shape as large as possible in the range in which the original support functions of the outer side rotation support part 44 and the inner side rotation support part 42 are kept.

Further, the cylindrical body 60 that is open toward the space between the X-ray source 36 and the X-ray detector 37 is disposed in the cavity 48 in a rotatable state around the rotation axis A with respect to the support part 30.

More specifically, the cylindrical body 60 is preferably configured so as to be disposed in the cavity 48 in a rotatable manner and form an inner space as large as possible. In this case, the cylindrical body 60 is formed in a bottomed cylindrical shape, and has an outer diameter slightly smaller than an inner diameter of the cavity 48 and a length in an axial direction that is substantially the same as a length of the cavity 48 in the axial direction. The cylindrical body 60 is disposed in the cavity 48 in the state where the center axis of the cylindrical body 60 is caused to substantially coincide with the rotation axis A.

Further, the cylindrical body 60 is held in a rotatable manner by the rotation support part 40 through bearings 70 (see FIGS. 7 and 8). The cylindrical body 60 rotates with respect to the support part 30. As described in a second preferred embodiment, which is related to the configuration of FIGS. 38 to 43, there is another configuration in which a cylindrical body 660 is fixed to the base 22 and the support part 30 rotates with respect to the cylindrical body 660. Accordingly, the cylindrical body rotates relatively with respect to the support part in the present application.

That is, the bearings 70 in a ring shape are provided between the bottom of the cylindrical body 60 and the bottom of the cavity 48. The bearing 70 includes an inner ring member 72 and an outer ring member 74 disposed in a rotatable manner around the inner ring member 72. Here, as the bearing 70, there is assumed a journal bearing and, in particular, a cross roller ring in which multiple cylindrical rollers are arranged so as to be orthogonal to each other along its circular arrangement direction. The use of the cross roller ring has an advantage that forces in various directions including the rotation axis direction and a radial direction thereof can be applied. The outer ring member 74 is fixed to the bottom of the cavity 48, more specifically, the bottom of the inner side rotation support part 42 through a screw or the like, and the inner ring member 72 is fixed to the bottom of the cylindrical body 60 through a screw or the like. Accordingly, the cylindrical body 60 is supported by the bottom of the rotation support part 40 in a rotatable manner through the bearings 70, and in a case of rotating the rotation support part 40 by driving of the rotary drive part 50, the cylindrical body 60 can be maintained in a state where it is not rotated. That is, even when the rotation support part 40 is rotated with respect to the base 22 to perform CT imaging, the cylindrical body 60 can be maintained in the state where it is not rotated with respect to the base 22.

If the rotation support part 40 is not in contact with the cylindrical body 60 when rotating, the friction force acts, whereby the cylindrical body 60 may also rotate along with the rotation of the rotation support part 40. However, in a case where a braking force is caused to act on the cylindrical body 60, the cylindrical body 60 can be maintained in the state where it does not rotate even when the rotation support part 40 rotates.

Note that the configuration example for supporting the cylindrical body 60 in a rotatable manner is not limited to the example above. The modification for achieving that purpose is described below.

Figure 2:
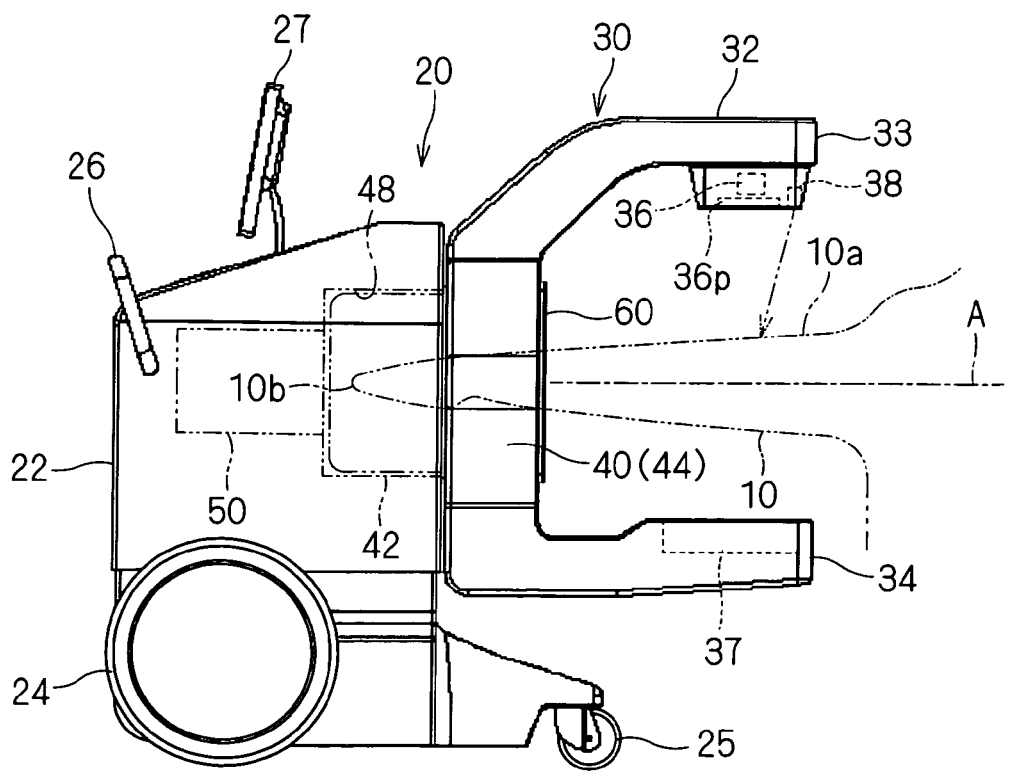
FIG. 2 is a side view showing the medical X-ray CT imaging apparatus according to the first preferred embodiment.
Figure 3:
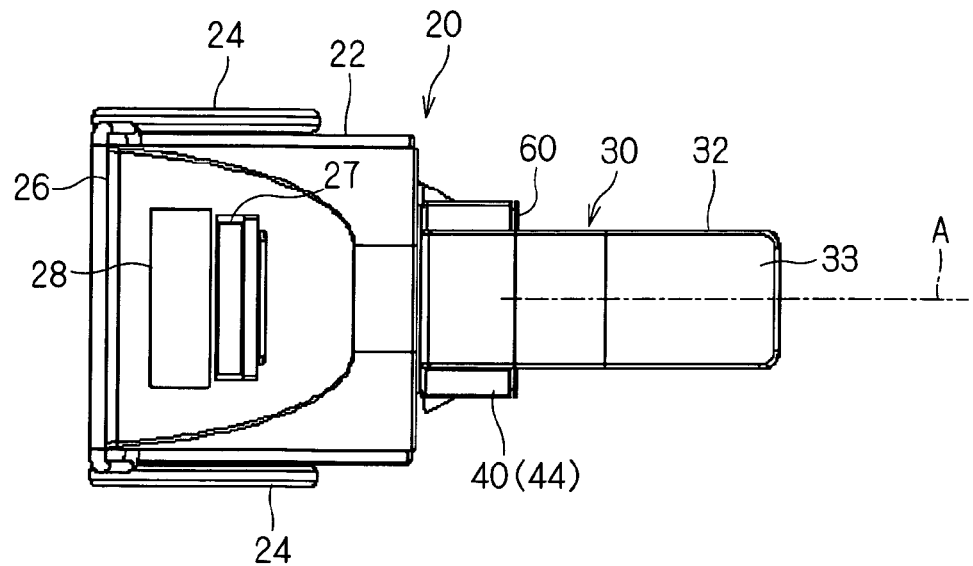
FIG. 3 is a plan view showing the medical X-ray CT imaging apparatus according to the first preferred embodiment.
Figure 4:
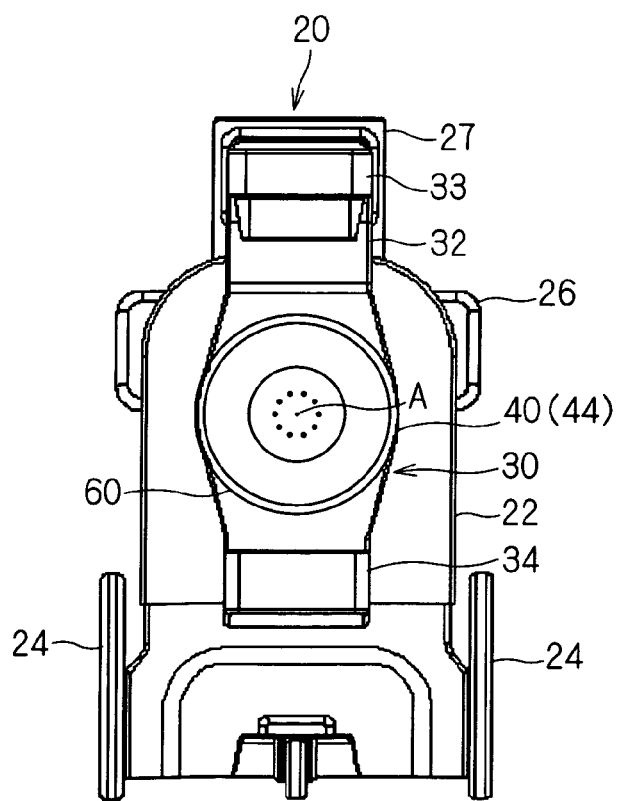
FIG. 4 is a front view showing the medical X-ray CT imaging apparatus according to the first preferred embodiment.
Figure 5:
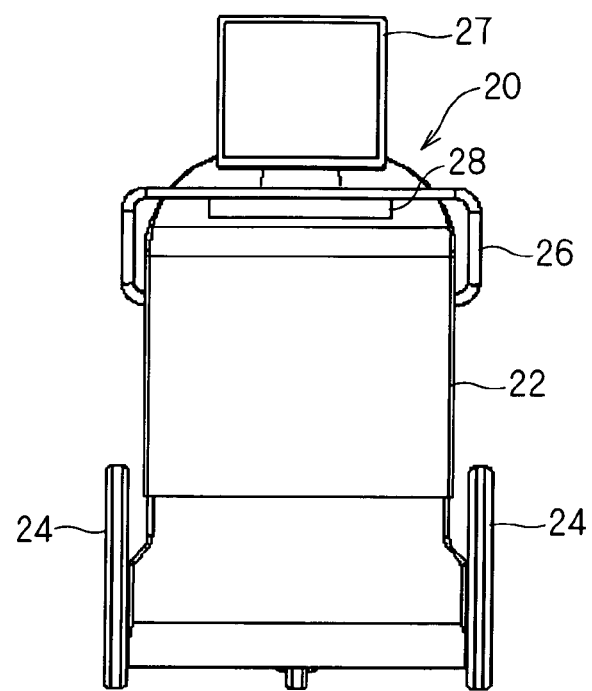
FIG. 5 is a rear view showing the medical X-ray CT imaging apparatus according to the first preferred embodiment.

In the medical X-ray CT imaging apparatus 20, in a case of imaging a part of a patient, for example, an upper arm 10a, an arm 10 of the patient is first disposed between the X-ray source 36 and the X-ray detector 37 along the rotation axis A (see FIG. 2). Then, in a state of keeping the arm 10 at a given position, the X-ray source 36 and the X-ray detector 37 are rotated around the rotation axis A by driving of the rotary drive part 50. Note that in the medical X-ray CT imaging apparatus 20, the X-ray source 36 and the X-ray detector 37 stand still in a direction along the rotation axis A during the rotation for X-ray CT imaging. That is, representing the height in the axial direction of the rotation axis A, the X-ray source 36 and the X-ray detector 37 rotate at the same height. Then, the processing for reconstructing an image is performed based on a signal in which the multiple pieces of projection data obtained in the X-ray detector 37 are reflected, to thereby obtain a CT image.

According to the medical X-ray CT imaging apparatus 20, the space of the cylindrical body 60 is formed at a position that is displaced from the imaged region between the X-ray source 36 and the X-ray detector 37 toward the side of the mounting ends of the pair of arm parts 33 and 34 along the rotation axis A. When a part of a patient is imaged, it is possible to dispose the part to be imaged between the X-ray source 36 and the X-ray detector 37 while disposing the portion in the vicinity of the spot to be imaged in the space of the cylindrical body 60 within the cavity 48. For example, in a case where the upper arm 10a is imaged as described above, it is possible to dispose the upper arm 10a between the X-ray source 36 and the X-ray detector 37 while disposing fingers 10b in the space within the cylindrical body 60. Then, in this state, the X-ray source 36 and the X-ray detector 37 are rotated by rotation of the support part 30 while stopping the rotation of the cylindrical body 60, to thereby perform X-ray CT imaging. As a result, there are fewer limitations when a part of a patient is disposed between the X-ray source 36 and the X-ray detector 37. Note that an example in which various parts of the patient are imaged is also described below in the modifications.

In particular, the cylindrical body 60 is held in a rotatable manner through the bearings 70 in the cavity 48 formed in the rotation support part 40. That is, the configuration for supporting the cylindrical body 60 in a rotatable manner is entirely incorporated between the cylindrical body 60 and the rotation support part 40. For this reason, fewer limitations are imposed on the layout of the rotary drive part 50 for rotatably driving the rotation support part 40. Accordingly, for example, the rotary drive part 50 is easily incorporated in the base 22 on the extension of the cylindrical body 60 in the axial direction, as described above. As a result, an area in which the base 22 is projected along the rotation axis A is reduced, which achieves miniaturization of the medical X-ray CT imaging apparatus 20.

Further, the cylindrical body 60 has a bottomed cylindrical shape, and thus various types of mechanisms, for example, the bearing 70, the rotary drive part 50 and the like are easily incorporated in the outer side portion of the bottom thereof, which makes it easy to, for example, simplify the configuration.

The fact that the bearings 70 and the rotary drive bearing parts 43 are concentrated in the vicinity of the bottom of the cavity 48, more specifically, the fact that in the bottom of the cavity, the bearings 70 are provided on the inner side of the cavity part 48 and the rotary drive bearing parts 43 are provided on the outer side thereof also contributes to a reduction in distance between the rotary drive part 50 and the opening end of the cavity 48. As a result, the medical X-ray CT imaging apparatus 20 is further miniaturized.

In a case where a part of a patient is disposed between the X-ray source 36 and the X-ray detector 37, the part to be imaged is positioned more accurately by checking the spot at which the arm 10 of the patient is irradiated with irradiation light from the positioning light irradiation part 38. As a result, a possibility of avoiding an imaging failure or re-imaging due to inappropriate positioning increases, leading to a less burden on the patient.

The X-ray regulating part 36P that regulates an irradiated region of an X-ray cone beam is provided in front of the X-ray source 36 in its irradiation direction, and thus local X-ray CT imaging can be performed in a more limited region, which is required for diagnosis, treatment or the like, which alleviates an exposure amount. As to the local X-ray CT imaging, there is used the X-ray CT imaging technology of imaging only a front tooth or a molar in dental surgery or imaging only a nose or ear in otolaryngology surgery, as disclosed in Japanese Patent No. 3919048 by the same applicant of the present application.

Further, the pair of wheels 24 and the auxiliary wheel 25 capable of changing a direction are provided to the lower part of the base 22 as the wheels capable of rolling on the floor, whereby the apparatus 20 can be moved easily to the location of the patient or the like. The apparatus 20 is also moved easily between examination rooms or between wards. Note that an angle for turning the support part 30 is not specifically limited in CT imaging by the apparatus 20, and CT imaging can be performed by, for example, turning the support part 30 around a part of the patient by 180° to 360°. In addition, there can be performed so-called offset CT imaging in which the X-ray source 36 and the X-ray detector 37 are arranged so as to obtain X-ray projection data of a half or more of the entire imaged region, though less than the entire imaged region, and the support part 30 is turned in the state where the X-ray source 36 and the X-ray detector 37 are opposed to each other, to thereby perform CT imaging. In the offset CT imaging, the support part 30 is turned 360° or more for obtaining projection data of 180° or more in the entire imaged region. According to the above-mentioned offset CT imaging, even in a case of an X-ray cone beam limited to imaging of a local region, it is possible to perform CT imaging of a region equal to or larger than the width of the cone beam, for example, a lumbar spiral of a patient. Therefore, it is possible to perform CT imaging of a large region while keeping an exposure amount of the patient.

Here, the configuration of the offset CT imaging is described in detail.

FIG. 9 schematically shows a state of normal CT imaging in a case of being viewed from the axial direction of the rotation axis A, and FIG. 10 schematically shows a state of offset CT imaging in a case of being viewed from the axial direction of the rotation axis A.

The "case of being viewed from the axial direction of the rotation axis A" may be a case of being viewed from a bottom side of the cavity 48 or a case of being viewed form an opening side of the cavity 48.

In the present application, CT imaging in which the entire imaged region is always within a range of being irradiated with an X-ray cone beam, not by offset CT imaging, is referred to as "normal CT imaging", whereas CT imaging by offset CT imaging is literally referred to as "offset CT imaging".

As shown in FIG. 9, in the normal CT imaging, an imaged region FE1 is always within the range of being irradiated with an X-ray cone beam CB during CT imaging. The X-ray detector 37 receives X-rays in the entire region within the range of being irradiated with the X-ray cone beam CB. The expansion of the X-ray cone beam CB when viewed from the axial direction of the rotation axis A is denoted by an angle AG1, and a symmetry axis of the angle AG1 of the expansion of the X-ray cone beam CB is denoted by BC1.

One boundary of the X-ray cone beam CB when viewed from the axial direction of the rotation axis A is denoted by a beam side part EG1, whereas the other boundary is denoted by a beam side part EG2. A portion of the X-rays that passes through the symmetry axis BC1 is denoted by a center beam XCB1. The expansion angle AG1 is equally divided into an angle AG2 and an angle AG3 by the symmetry axis BC1. Needless to say, the angle AG2 is equal to the angle AG3.

A periphery of the imaged region FE1 is completely round, and the center of the imaged region FE1 is a center of imaged region AC1.

Considering the support part 30 as a mechanical component, the support part 30 has a mechanically turning axis that is rotatively driven by the rotary drive part 50. In terms of a member, the inner side rotation support part 42 functions as a mechanically turning axis as a member applied with a rotational force from the rotary drive part 50. In the example shown in FIG. 9, an axis center of the mechanically turning axis coincides with the center of imaged region AC1 in position.

During CT imaging, the X-ray source 36 and the X-ray detector 37 turn with the imaged region FE1 being sandwiched therebetween while the X-ray source 36 irradiates the X-ray cone beam CB, and the X-ray detector 37 moves from a starting position LA1 to the position LA1 via a position LA2 where the X-ray detector 37 turns 90, a position LA3 where the X-ray detector 37 turns 180°, and a position LA4 where the X-ray detector 37 turns 270°.

In the normal CT imaging, projection data in a range in which there is no problem for obtaining a CT image by reconstruction at a position where the X-ray detector 37 moves to the position LA3, and thus CT imaging may be ended when the X-ray detector 37 moves to the position LA3.

During CT imaging, the center beam XCB1 always passes through the center of imaged region AC1, and the beam side part EG1 and the beam side part EG2 are always in contact with a periphery of the imaged region FE1.

As shown in FIG. 10, in the offset CT imaging, only part of the imaged region FE2 is within the range of being irradiated with the X-ray cone beam CB during CT imaging. The X-ray detector 37 receives X-rays in the entire region within the range of being irradiated with the X-ray cone beam CB. The expansion of the X-ray cone beam CB when viewed from the axial direction of the rotation axis A is denoted by an angle AG4, and a symmetry axis of the expansion angle AG4 of the X-ray cone beam CB is denoted by BC2.

One boundary of the X-ray cone beam CB when viewed from the axial direction of the rotation axis A is denoted by a beam side part EG3, whereas the other boundary is denoted by a beam side part EG4. A portion of the X-rays that passes through the symmetry axis BC2 is denoted by a center beam XCB2. The expansion angle AG4 is equally divided into an angle AG5 and an angle AG6 by the symmetry axis BC2. Needless to say, the angle AG5 is equal to the angle AG6.

A periphery of the imaged region FE2 is completely round, and the center of the imaged region FE2 is a center of imaged region AC2. An axis center of the mechanically turning axis of the support part 30 coincides with the center of imaged region AC2 in position.

During CT imaging, the X-ray source 36 and the X-ray detector 37 turn with the imaged region FE2 being sandwiched therebetween while the X-ray source 36 irradiates the X-ray cone beam CB, and the X-ray detector 37 moves from a starting position LB1 to the position LB1 via a position LB2 where the X-ray detector 37 turns 90°, a position LB3 where the X-ray detector 37 turns 180°, and a position LB4 where the X-ray detector 37 turns 270°.

In the offset CT imaging, the symmetry axis BC2 of the X-rays does not pass through the center of imaged region AC2 in the imaged region FE2 but moves on an arc CL1 with the center of imaged region AC2 being the center, to thereby perform imaging in a wide range. In a case of magnifying the imaged region most, an X-ray that passes through the center of a region of interest of a subject is caused to enter the end of a two-dimensionally detection surface of an X-ray detector.

In the example shown in FIG. 10, of the beam side part EG3 and the beam side part EG4, only the beam side part EG3 is always in contact with a periphery of the imaged region FE2, while the beam side part EG4 is always on an inner side than the periphery of the imaged region FE2.

The regions imaged by the X-ray detector 37 at respective timings do not include the entire imaged region, but owing to 360 rotation around the subject, the data required to CT image reconstruction is collected as to an imaged region larger than the regions imaged at respective timings. Needless to say, imaging may be performed more than 360°.

Figure 1:
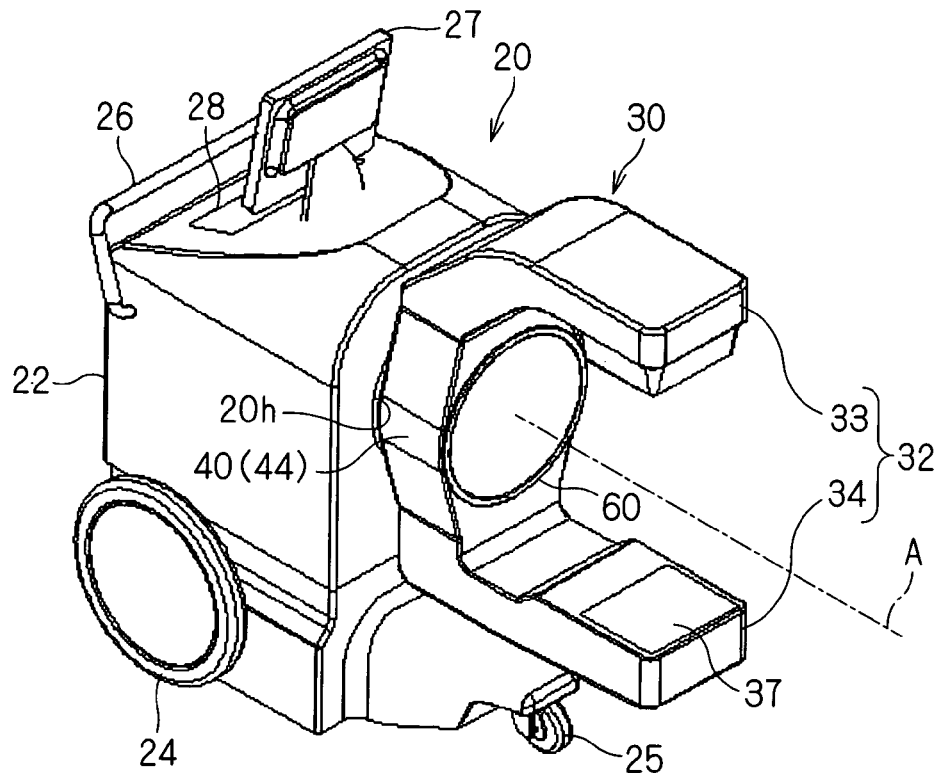
FIG. 1 is a perspective view showing a medical X-ray CT imaging apparatus according to a first preferred embodiment.
Figure 11:
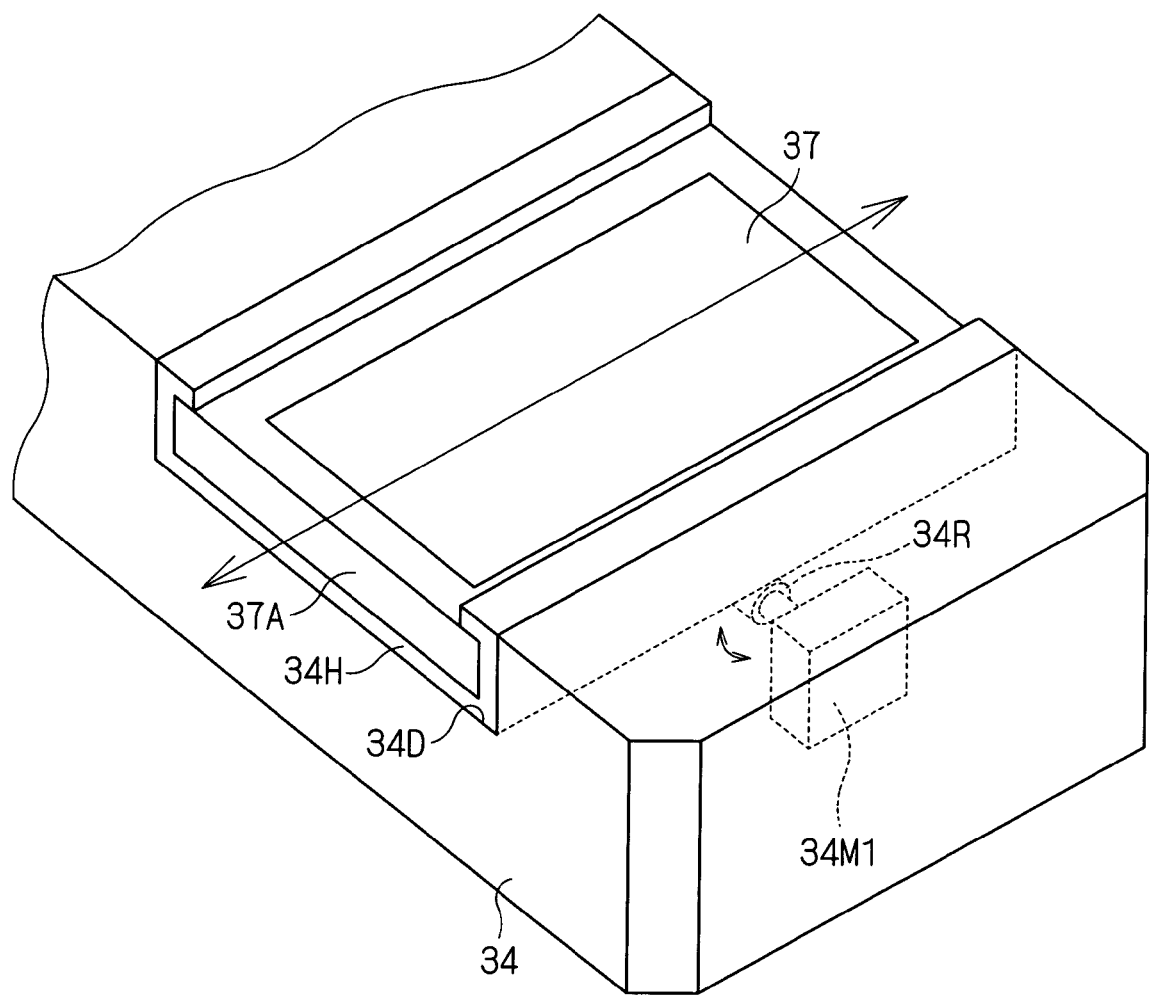
FIG. 11 is a view showing a specific configuration example where the normal CT imaging and the offset CT imaging can be switched.
Figure 12:
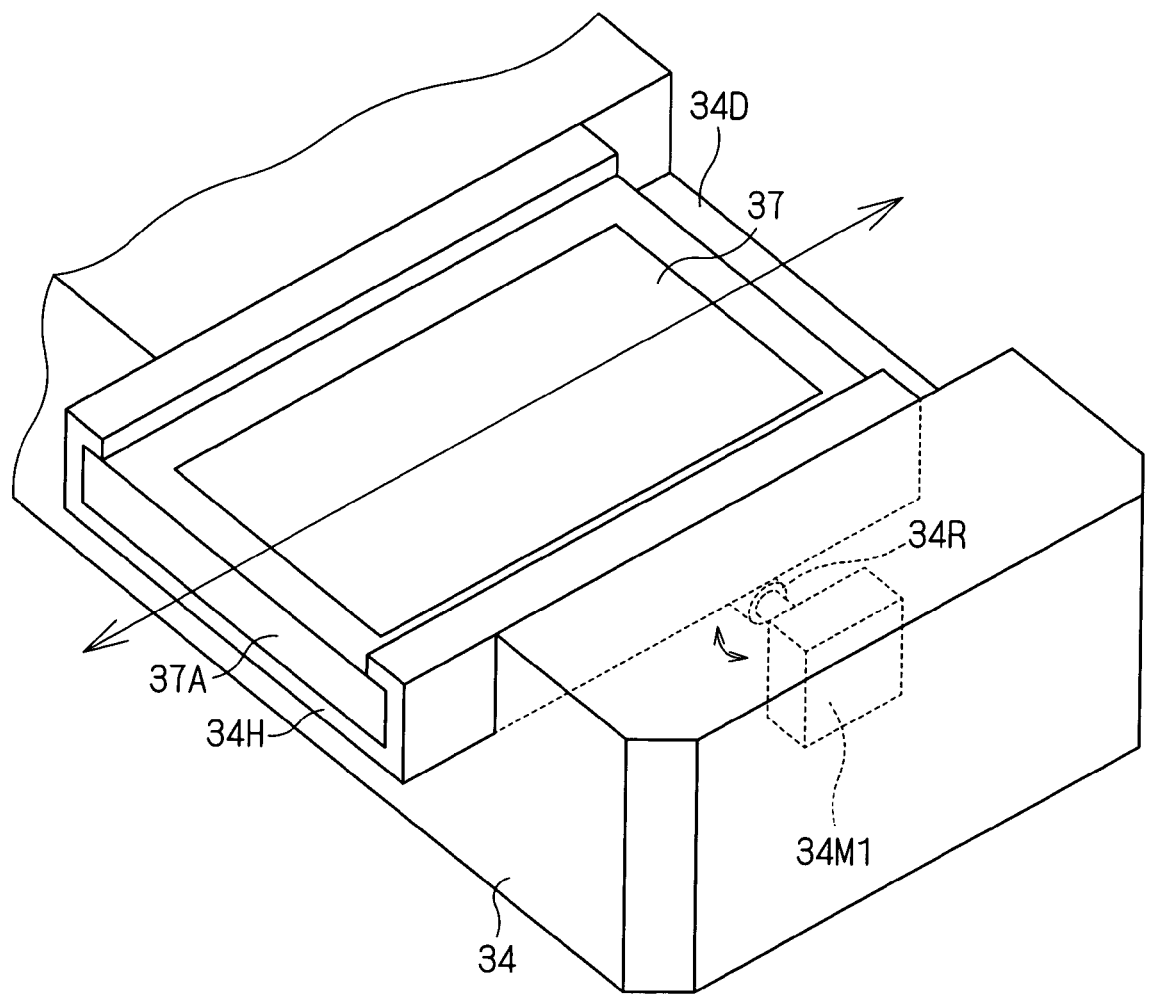
FIG. 12 is a view showing another specific configuration example where the normal CT imaging and the offset CT imaging can be switched.

FIGS. 11 and 12 show specific configuration examples in which normal CT imaging and offset CT image can be switched in the medical X-ray CT imaging apparatus of FIG. 1. FIG. 11 shows a state of the normal CT imaging, while FIG. 12 shows a state of the offset CT imaging.

The normal CT imaging is executed in a normal CT imaging mode, while the offset CT imaging is executed in an offset CT imaging mode.

The arm part 34 includes an X-ray detector holder guiding part 34D. An X-ray detector holder 34H is fitted with the X-ray detector holder guiding part 34D. Owing to the above-mentioned movable fitting structure, the X-ray detector holder 34H can be displaced in a direction parallel to a tangent in contact with an arc (arc when viewed from the rotation axis A) taken by the X-ray detector 37 (end of the arm part 34) as a result of the turning of the support part 30.

Note that there is provided a guiding mechanism (not shown) between the X-ray detector holder guiding part 34D and the X-ray detector holder 34H so that the X-ray detector holder 34H can be displaced without being detached from the X-ray detector holder guiding part 34D.

The X-ray detector holder 34H is configured so as to hold the X-ray detector 37. A surface of the X-ray detector holder 34H that is opposed to the X-ray source 36 is open so as not to interrupt an X-ray detection surface of the X-ray detector 37.

A driving motor 34M1 is fixed to the inside of the arm part 34, and a roller 34R is provided to a driving axis thereof. The roller 34R abuts against a rear surface of the X-ray detector holder 34H. The X-ray detector holder 34H is configured so as to be displaced in the above-mentioned direction parallel to the tangent owing to the rotation of the roller 34R by driving of the driving motor 34M1.

The normal CT imaging shown in FIG. 9 is performed by positioning the X-ray detector 37 as shown in FIG. 11, whereas the offset CT imaging shown in FIG. 10 is performed by positioning the X-ray detector 37 as shown in FIG. 12.

Between the case where the normal CT imaging of FIG. 9 is performed and the case where the offset CT imaging of FIG. 10 is performed, a position of an opening for CT imaging of the X-ray regulating part 36P may be moved correspondingly to a moving amount of the X-ray detector 37. That is, an irradiation direction of the X-ray cone beam CB is changed such that the X-ray detector 37 receives the X-rays in the entire region within the range of being irradiated with the X-ray cone beam CB even when the position of the X-ray detector 37 is displaced.

In the present application, the mechanism that includes the X-ray detector holder guiding part 34D, the X-ray detector holder 34H and the driving motor 34M1 and enables the offset CT imaging as described above is referred to as an offset CT imaging mechanism.

Although the offset CT imaging mechanism of this example has the configuration capable of switching the normal CT imaging and the offset CT imaging, an X-ray CT imaging apparatus dedicated for offset CT imaging may be used as the configuration in which the X-ray detector 37 is fixed to the position for offset CT imaging from the beginning.

While FIGS. 11 and 12 show the offset CT imaging mechanism with a simple structure for easy understanding, in reality, any mechanism may be used as long as it enables the offset CT imaging. The offset CT imaging mechanism may be added to any example in the present application.

FIG. 13 shows another example in which an imaged region is changed. In FIG. 13, the arm part 34 is partially deformed in the medical X-ray CT imaging apparatus of FIG. 1.

The arm part 34 includes an arm base part 34B fixed to the rotation support part 40 and a moving arm part 34T capable of displacing with respect to the arm base part 34B.

The moving arm part 34T is capable of displacing in a direction so as to be close to or apart from the X-ray source 36 by a guiding mechanism 34N.

Displacement driving of the moving arm part 34T is performed by a driving motor 34M2. The driving motor 34M2 is fixed to the arm base part 34B. A screw shaft part 34MA is connected to a rotation axis of the driving motor 34M2 directly or indirectly, whereby the screw shaft part 34MA is rotatively driven by driving of the driving motor 34M2.

A female screw member 34TS is fixed to the moving arm part 34T, and the screw shaft part 34MA is screwed with the female screw member 34TS. Owing to the rotary drive of the screw shaft part 34MA, the female screw member 34TS is displacement-driven in the direction so as to be close to or apart from the X-ray source 36. Owing to the displacement driving of the female screw member 34TS, the moving arm part 34T is displacement-driven in the direction so as to be close to or apart from the X-ray source 36.

In the example of FIG. 13, the position of the X-ray detector 37 at a position LT1 is regarded as a home position, and a position LT2 close to the X-ray source 36 is regarded as an imaged region magnifying position. Needless to say, the position of the X-ray detector 37 at the position LT2 may be regarded as the home position, and the position LT1 apart from the X-ray source 36 may be regarded as an imaged region reducing position. Alternatively, a middle point between the position LT1 and the position LT2 may be regarded as the home position, and displacement may be made to the position LT1 as well as the position LT2. The home position that is the initial position, a moving direction from the position and the like are set freely.

Between the case where the CT imaging is performed by the X-ray detector 37 at the position LT1 and the case where the CT imaging is performed by the X-ray detector 37 at the position LT2, a width of an opening for CT imaging of the X-ray regulating part 36P may be changed correspondingly to an amount by which the X-ray detector 37 becomes close thereto or apart therefrom. That is, the irradiation width of the X-ray cone beam CB is changed such that the X-ray detector 37 receives the X-rays in the entire region within the range of being irradiated with the X-ray cone beam CB even when the position of the X-ray detector 37 is displaced. In this case, when CT imaging is performed by the X-ray detector 37 at the position LT2, the width of the opening for CT imaging of the X-ray regulating part 36P is larger compared with the case where CT imaging is performed by the X-ray detector 37 at the position LT1.

The mechanism that includes the arm base part 34B, the moving arm part 34T, the driving motor 34M2, the screw shaft part 34MA and the female screw member 34TS and enables a change in magnification is referred to as a magnification changing mechanism in the present application.

Figure 14:
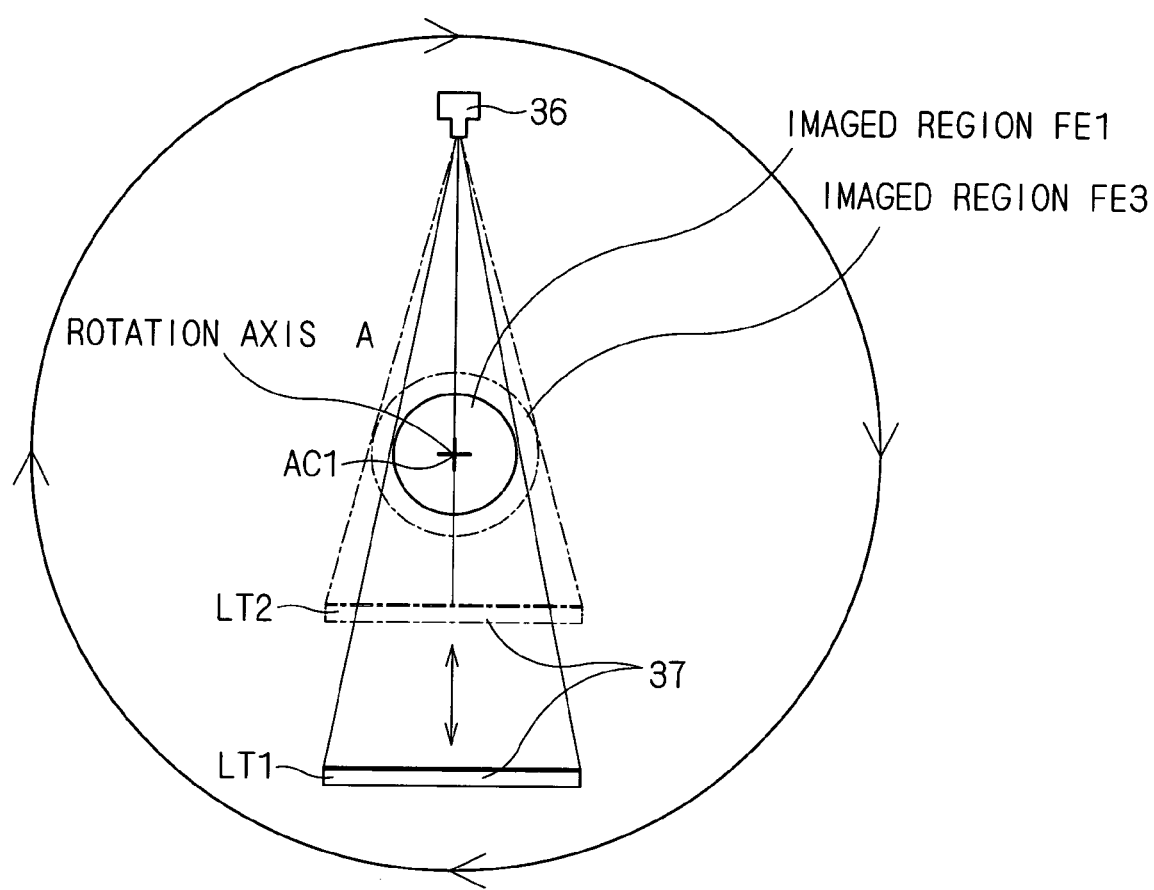
FIG. 14 schematically shows CT imaging in the example shown in FIG. 13.

FIG. 14 schematically shows CT imaging when viewed from the axial direction of the rotation axis A in the example of FIG. 13.

CT imaging in the imaged region FE1 can be performed in a case where the X-ray detector 37 is located at the position LT1, whereas CT imaging in the imaged region FE3 can be performed in a case where the X-ray detector 37 is positioned at the position LT2. The magnification is smaller by an amount that the X-ray detector 37 at the position LT2 is close to the subject, whereby it is possible to perform CT imaging in a wider range compared with the X-ray detector 37 at the position LT1. The magnification is larger by an amount that the X-ray detector 37 at the position LT1 is far from the subject, whereby CT imaging is performed in a narrower range compared with the X-ray detector 37 at the position LT2. Therefore, the X-ray detector 37 at the position LT1 is preferably used in a case where a small area to be observed is displayed to be large for observation.

Incidentally, the magnification is calculated from DTA/DTB where DTA represents a distance between an X-ray focal point of the X-ray source 36 and an X-ray detection surface of the X-ray detector 37 and DTB represents a distance between the X-ray focal point of the X-ray source 36 and the center of imaged region AC1.

In the preferred embodiment in the case of the configuration of FIG. 13, the offset CT imaging mechanisms that have the configurations of FIGS. 11 and 12 may be further provided and, in that case, the degree of freedom in scaling of the imaged region is enhanced.

Although FIG. 13 shows the magnification changing mechanism of a simple structure for easy understanding, in actuality, any mechanism may be used as long as it enables a change in magnification. For example, the magnification may be changed by moving the X-ray source side so that the X-ray detector is relatively close to or apart from the X-ray source. Further, the magnification changing mechanism may be added to any example of the present application.

Hereinafter, various modifications based on the first preferred embodiment are described. In the description of the various modifications below, similar elements to those described in the first preferred embodiment are denoted by like reference symbols and description thereof is omitted, but a difference is mainly described.

(First Modification)

Figure 15:
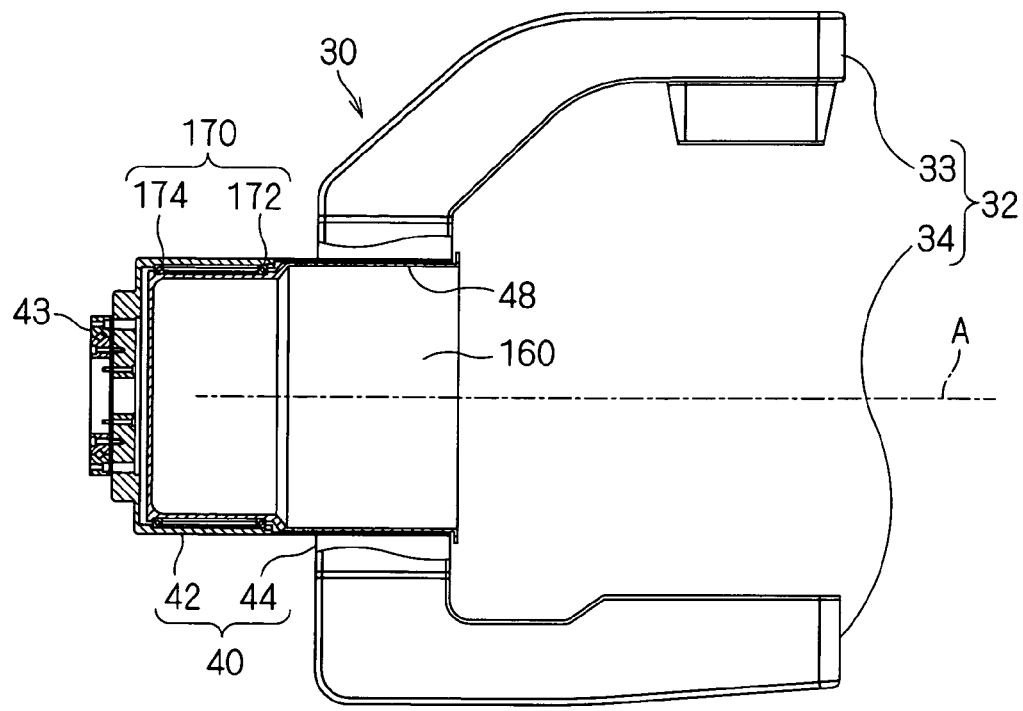
FIG. 15 is a cross-sectional view showing a rotation support part and a cylindrical body according to a first modification of the first preferred embodiment.
Figure 16:
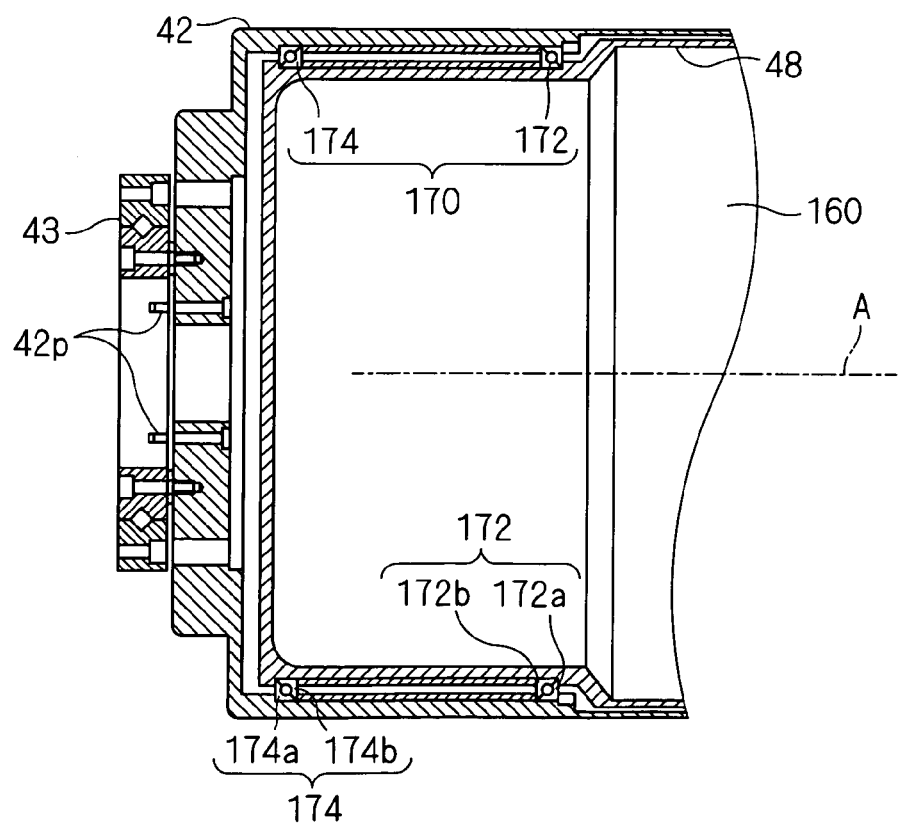
FIG. 16 is a partially enlarged cross-sectional view of FIG. 15.

In the first modification, a modified example of the bearing 70 according to the first preferred embodiment is described. FIGS. 15 and 16 are cross-sectional views of main parts showing the rotation support part 40 and a cylindrical body 160, which show a bearing 170 according to the first modification.

The cylindrical body 160 is configured to have a smaller (in this case, slightly smaller) diameter of the bottom side portion compared with the cylindrical body 60.

The bearing 170 is provided between an outer periphery of the cylindrical body 160 and an inner periphery of the cavity 48 of the rotation support part 40, and includes an opening side bearing part 172 located on the opening side of the cylindrical body 160 and a bottom side bearing part 174 located on the bottom side thereof.

The opening side bearing part 172 is configured by connecting an outer ring member 172a and an inner ring member 172b in a relatively rotatable manner through, for example, a rolling element such as a ball. The bottom side bearing part 174 is configured by connecting an outer ring member 174a and an inner ring member 174b in a relatively rotatable manner through, for example, a rolling element such as a ball.

Further, the opening side bearing part 172 and the bottom side bearing part 174 are matched angular contact ball bearings that are configured to receive a rotational load and a thrust load applied in the rotation axis A direction. Moreover, the opening side bearing part 172 and the bottom side bearing part 174 are mounted in combination in a direction in which they withstand a moment load applied in a direction orthogonal to the rotation axis A. The outer ring members 172a and 174a are fixed to an inner peripheral surface of the cavity 48 of the rotation support part 40, whereas the inner ring members 172b and 174b are fixed to an outer peripheral surface of the cylindrical body 160. In this manner, the cylindrical body 160 is supported in a relatively rotatable manner, by the angular contact ball bearings that are combined for withstanding various loads, with respect to the rotation support part 40 in the cavity 48.

According to the first modification, similar operation and effect as in the first preferred embodiment are obtained as well. In the first modification, a sufficient space of the cavity 48 is secured by the inner side itself of the inner ring member 172a, and thus the bearing itself acts as the cavity 48, to thereby contribute to miniaturization of the medical X-ray CT imaging apparatus 20.

As described in the first modification, various modes are assumed as the configuration in which a cylindrical body is supported in a rotatable manner. For example, as the bearing that supports a cylindrical body in a rotatable manner, a journal bearing or an angular contact ball bearing may be used. In particular, as described in first preferred embodiment, with the use of the journal bearings provided to the bottom of the cylindrical body, the cylindrical body can be supported with a simple configuration such that a diameter of the inner space of the cylindrical body is made as large as possible. Alternatively, as described in the first modification, with the use of the angular contact ball bearings that support the cylindrical body on its outer periphery in a rotatable manner, it is possible to effectively suppress the center axis of the cylindrical body from being decentered or tilted. Further, the bearing to be used may be a sliding bearing or rolling bearing and, in a case of the rolling bearing, it may be a ball bearing or roller bearing.

(Second Modification)

Figure 17:
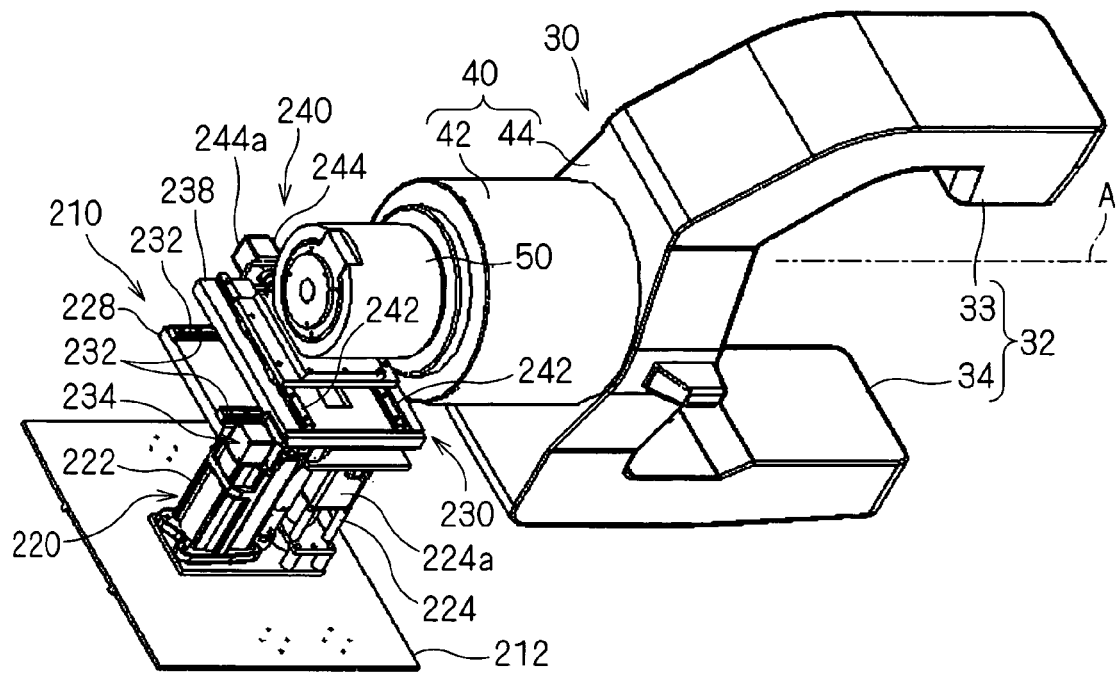
FIG. 17 is a perspective view showing a moving mechanism part according to a second modification of the first preferred embodiment.
Figure 18:
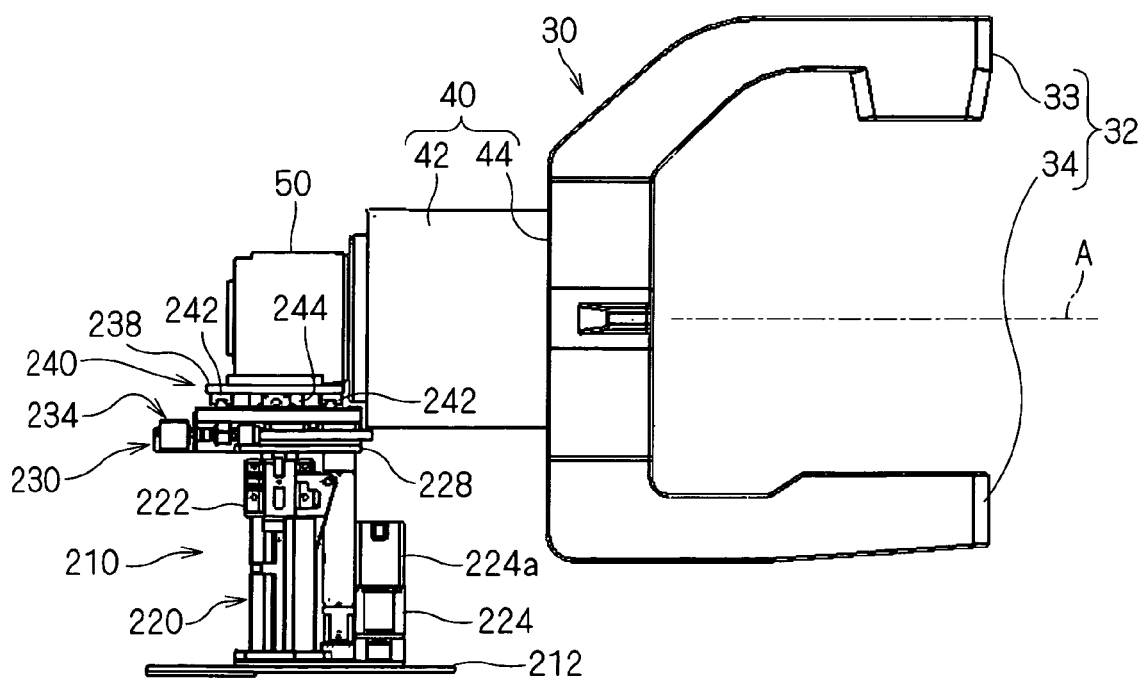
FIG. 18 is a side view showing the moving mechanism part according to the second modification of the first preferred embodiment.
Figure 19:
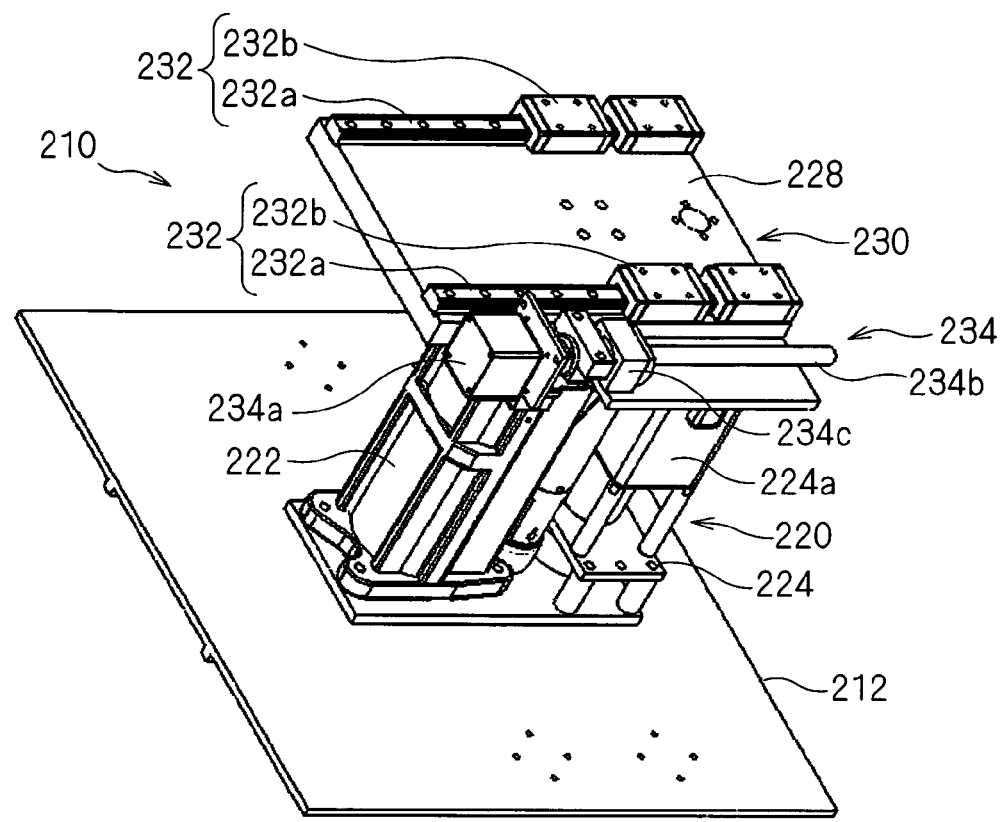
FIG. 19 is a perspective view mainly showing a Z direction moving mechanism part and a Y direction moving mechanism part of the moving mechanism part according to the second modification of the first preferred embodiment.
Figure 20:
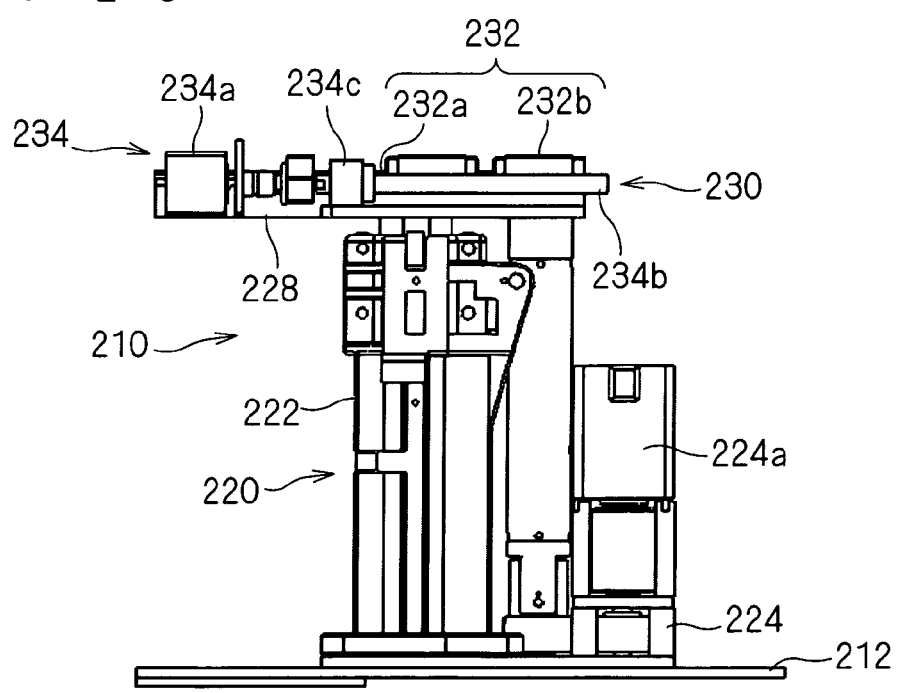
FIG. 20 is a side view mainly showing the Z direction moving mechanism part and the Y direction moving mechanism part of the moving mechanism part according to the second modification of the first preferred embodiment.
Figure 21:
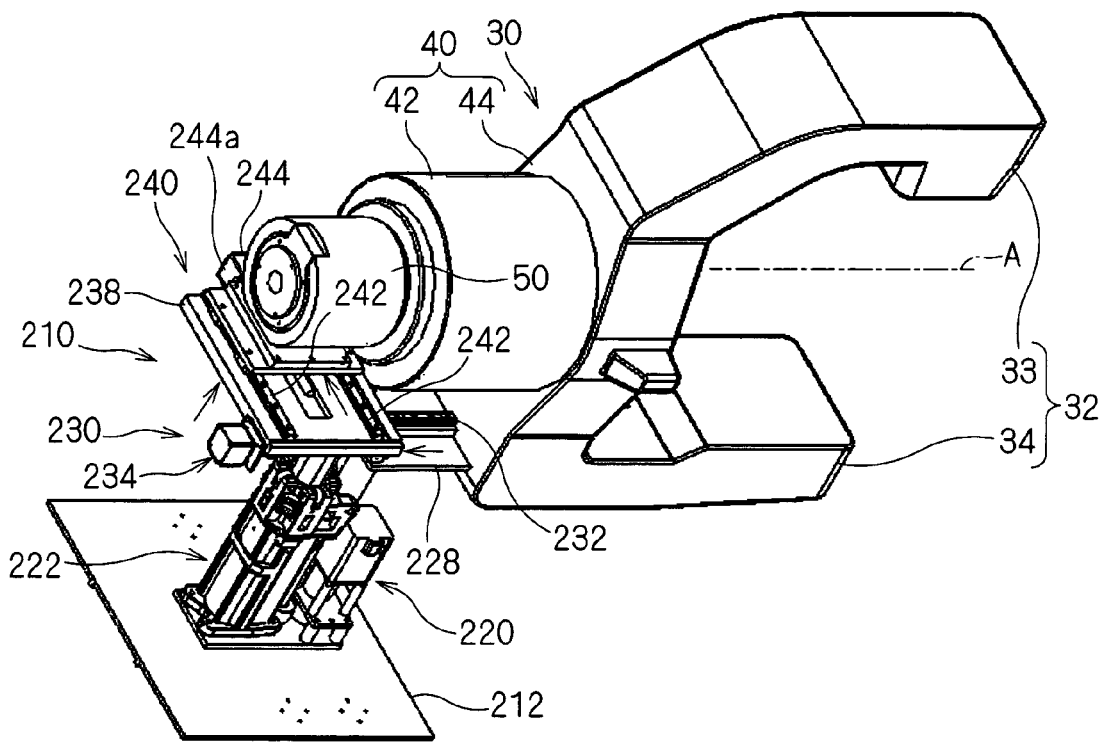
FIG. 21 is a perspective view showing a state in which the support part is moved from the state shown in FIG. 17.
Figure 22:
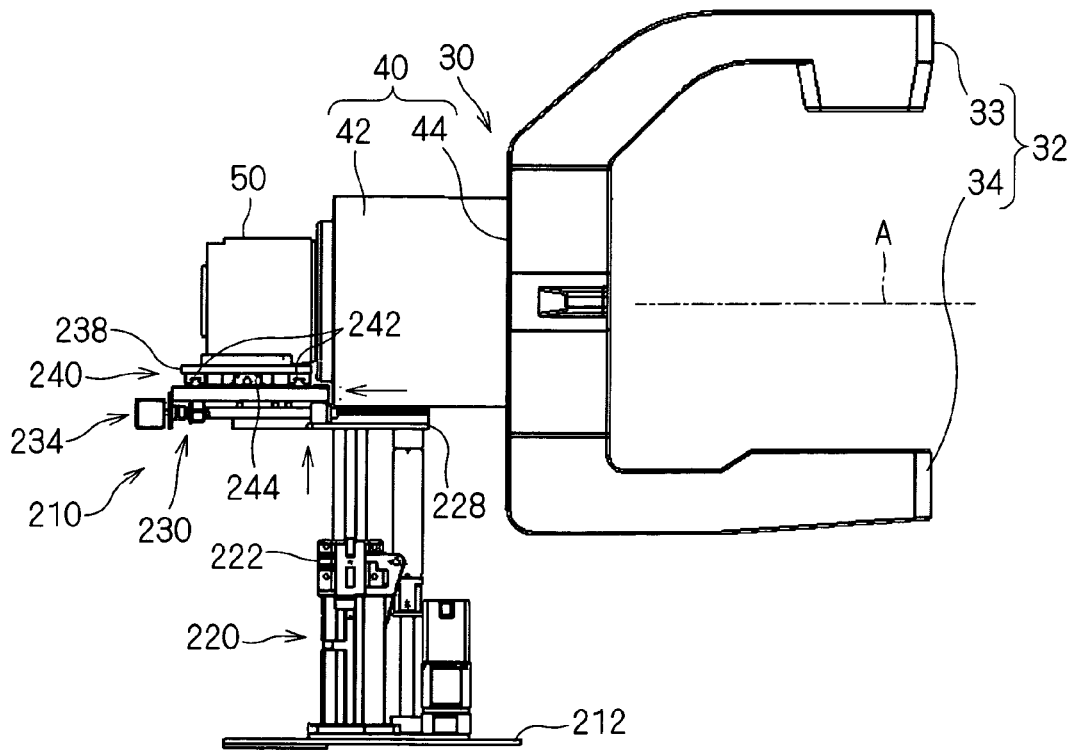
FIG. 22 is a side view showing a state in which the support part is moved from the state shown in FIG. 18.

In a second modification, description is given of an example in which the support part 30 is supported in a movable manner. FIGS. 17 and 18 are views showing a moving mechanism part 210 that supports the support part 30 in a movable manner, FIGS. 19 and 20 are views in which the support part 30, the rotary drive part 50 and a drive part mounting plate 238 are omitted from the FIGS. 17 and 18, and FIGS. 21 and 22 are views showing a state in which the support part 30 is moved from the state shown in FIGS. 17 and 18. In FIGS. 21 and 22, the direction in which the support part 30 is moved from the state shown in FIGS. 17 and 18 is indicated by an arrow. Note that in the description of the moving mechanism part 210, the rotation axis A direction and a vertical direction are referred to as a Y direction and a Z direction, respectively, and a direction orthogonal to both the Y direction and the Z direction is referred to as an X direction.

The moving mechanism part 210 includes a Z direction moving mechanism part 220 that moves the support part 30 along the Z direction, a Y direction moving mechanism part 230 that moves the support part 30 along the Y direction, and an X direction moving mechanism part 240 that moves the support part 30 along the X direction. Note that there is formed a sufficiently large mounting hole part 22h in the base 22 so as to move the support part 30.

The Z direction moving mechanism part 220 is fixed to a base plate 212 fixed to the bottom of the base 22 in a standing manner. The Z direction moving mechanism part 220 includes a Z direction guide part 222 that supports an elevating plate 228 in a substantially horizontal position so as to move in the Z direction and a Z direction drive part 224 that moves and drives the elevating plate 228 in the Z direction. The Z direction guide part 222 is capable of employing, for example, the configuration in which an inner rectangular tube is inserted into an outer rectangular tube that is vertically arranged on the base plate 212 so as to make a sliding movement and the elevating plate 228 is fixed to the upper end of the inner rectangular tube in a substantially horizontal position. The Z direction drive part 224 includes a motor 224a, and moves and drives the elevating plate 228 in the Z direction by a rotary driving force of the motor 224a. As the mechanism that transmits the rotary driving force of the motor 224a as the force for driving the elevating plate 228 in an elevating manner, for example, the following configurations are used: the configuration in which a female screw member that is integrated with the elevating plate 228 is screwed with a ball screw shaft vertically arranged in a rotatable manner along the Z direction, and the ball screw shaft is rotated by the motor 224a, to thereby drive the female screw member and the elevating plate 228 in an elevating manner, and the configuration in which the elevating plate 228 is driven in an elevating manner by driving of a chain that is circularly and rotatively driven by the motor 224a. The elevating plate 228 may be driven in an elevating manner by a known hydraulic cylinder and a piston.

The Y direction moving mechanism part 230 includes Y direction guide parts 232 provided on the elevating plate 228 and a Y direction drive part 234 that moves and drives the drive part mounting plate 238 in the Y direction. The Y direction guide part 232 includes a guide ridge part 232a disposed on the elevating plate 228 along the Y direction and movable receiving parts 232b disposed so as to freely move on the guide ridge part 232a (see FIG. 19). In this case, two Y direction guide parts 232 are provided with an interval therebetween in the X direction on the elevating plate 228. The drive part mounting plate 238 is fixed to the movable receiving parts 232b with screws or the like, whereby the drive part mounting plate 238 is supported so as to move in the Y direction on the elevating plate 228. In addition, the Y direction drive part 234 includes a motor 234a, a ball screw shaft part 234b, and a female screw member 234c. The motor 234a is mounted onto and fixed to one side part of the drive part mounting plate 238, and the ball screw shaft part 234b is rotatably disposed to one side part of the drive part mounting plate 238. The ball screw shaft 234b is connected to a rotation axis of the motor 234a directly or through a transmission member such as a gear and a belt. The female screw member 234c is screwed with the ball screw shaft 234b and is fixed to the elevating plate 228 with screwing or the like. The ball screw shaft 234b is rotatively driven by the motor 234a to move and drive the ball screw shaft 234b, the motor 234a and the drive part mounting plate 238 along the Y direction with respect to the female screw member 234c and the elevating plate 228.

The X direction moving mechanism part 240 includes X direction guide parts 242 provided on the drive part mounting plate 238 and an X direction drive part 244 that moves and drives the rotary drive part 50 in the X direction. The X direction guide part 242 is configured in substantially the same manner as the Y direction guide part 232 except for that the direction for movable guiding is the X direction, and supports the rotary drive part 50 in a movable manner in the X direction. Further, the X direction drive part 244 is configured in the same manner as the Y direction drive part 234 except for that the direction for movable driving is the X direction, and is configured to move and drive, the rotary drive part 50 along the X direction by driving of the motor 244a. Although partially not shown in the drawings, the motor 244a is mounted onto and fixed to the bottom of the rotary drive part 50 formed in a plate shape, which drives a screw shaft part screwed with the female screw member fixed to the drive part mounting plate 238. Upon driving of the motor 244a, a movable receiving part that is guided by the X direction guide part 242 and is fixed to the bottom of the rotary drive part 50 moves in the X direction.

Note that when the casing that is a fixing area of the rotary drive part 50 is fixed to a vertical fixing plate (not shown) vertically arranged on the drive part mounting plate 238 with screws or the like, a stator of the rotary drive part 50 that is, for example, an electric motor is fixed so as not to rotate, which enables the rotor of the rotary drive part 50 to rotate stably.

Further, as described in the first preferred embodiment, the support part 30 is supported so as to be rotatively driven by the rotary drive part 50. The rotary drive part 50 and the support part 30 are moved and driven in the Z direction (vertical direction) by driving of the Z direction moving mechanism part 220, are moved and driven in the Y direction (rotation axis A direction) by driving of the Y direction moving mechanism part 230, and are moved and driven in the X direction (horizontal direction) by driving of the X direction moving mechanism part 240.

That is, in the moving mechanism part 210, the Z direction moving mechanism part 220 and the X direction moving mechanism part 240 constitute a two-axially moving mechanism part that enables the support part 30 to move along two axial directions (X direction and Z direction) that are orthogonal to the rotation axis A and are orthogonal to each other. In addition, the Y direction moving mechanism part 230 constitutes a rotation axis direction moving mechanism part that enables the support part 30 to move along the rotation axis A direction (Y direction).

Note that driving of the moving mechanism part 210 is controlled, for example, based on an instruction issued by a user to the input part 28 under the control of the CT imaging processing unit.

That is, in the state where a part of a patient is disposed at a given position between the X-ray source 36 and the X-ray detector 37, the support part 30 and the X-ray source 36 and the X-ray detector 37 that are supported by the support part 30 are moved in the X direction, the Y direction and the Z direction such that the part to be imaged is disposed in a predetermined imaged region between the X-ray source 36 and the X-ray detector 37.

As a result, it is possible to easily adjust positions of the X-ray source 36 and the X-ray detector 37 with respect to a certain part to be imaged without causing a patient to move, which alleviates a burden on the patient. Further, according to this second modification, various types of CT imaging can be performed. For example, bilaterally symmetric positions of a part of a patient can be imaged successively in such a manner that the support part 30 is turned 180° to perform CT imaging of a right knee, the support part 30 is moved in the X direction, and then the support part 30 is turned 180° in an opposite direction to perform CT imaging of a left knee. Further, for example, CT imaging of part of an arm of a patient is performed, CT imaging of a portion of the arm that is continuous from the last imaged spot is performed after the support part 30 is moved in the Y direction, and image processing for connecting the obtained CT images is performed. Accordingly, it is possible to perform CT imaging of a part of a patient that has a length along the rotation axis A direction, such as an ulna of an arm of a patient.

Note that the moving mechanism part 210 is not required to have the configuration so as to move the support part 30 in all three axial directions. For example, the configuration may be made such that the Y direction moving mechanism part 230 is omitted, and the Z direction moving mechanism part 220 and the X direction moving mechanism part 240 cause the support part 30 to move in the direction orthogonal to the rotation axis A. Alternatively, the configuration may be made such that the Z direction moving mechanism part 220 and the X direction moving mechanism part 240 are omitted, and the Y direction moving mechanism part 230 causes the support part 30 to move in the rotation axis A direction.

Further, while the support part 30 is moved by driving of the motor in the description above, the support part 30 may be moved with a manually operated handle or the like.

Third Modification

In a third modification, description is given of the configuration for holding a part of a patient that is imaged in CT imaging at a given position.

Figure 23:
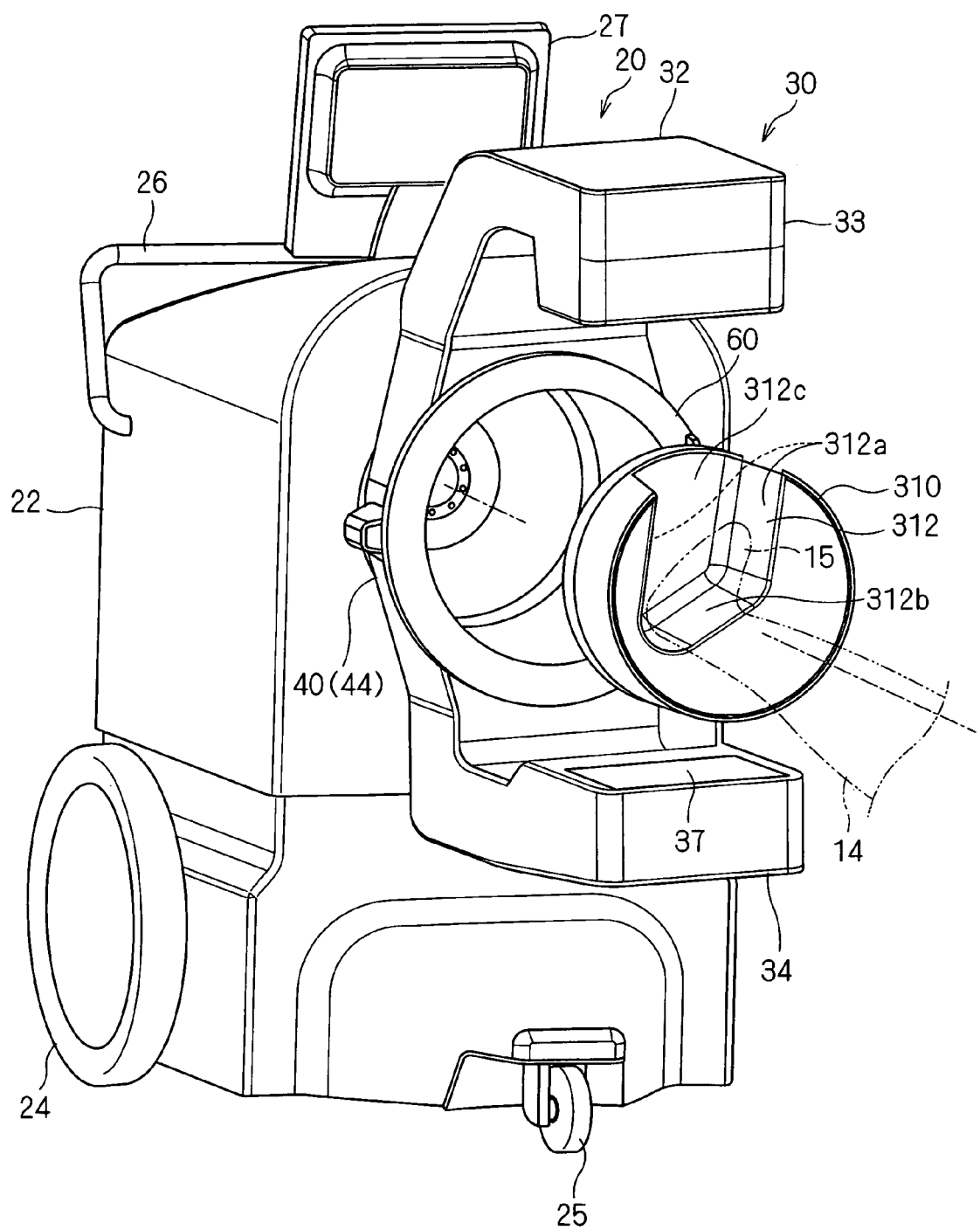
FIG. 23 is a perspective view showing an example in which a holding part is provided in a cylindrical body according to a third modification of the first preferred embodiment.

FIG. 23 is a perspective view showing an example in which a holding part 310 is provided in the cylindrical body 60.

The holding part 310 is a member that holds part of a patient in the cylindrical body 60 and, in this case, has a substantially cylindrical shape where a length dimension in an axial direction is approximately equal to the length of the inner space of the cylindrical body 60 in the axial direction, and a diameter is approximately equal to a diameter of the inner space of the cylindrical body 60. The holding part 310 is detachably disposed in the cylindrical body 60 at a fixed position and in a fixed position with respect to the cylindrical body 60. In this case, the holding part 310 is formed of an elastic member such as an elastomeric resin, and the holding part 310 is fitted into the cylindrical body 60 while being elastically compressed, with the result that the holding part 310 is disposed at the fixed position and in the fixed position in the cylindrical body 60. Alternatively, the holding part 310 may be disposed at the fixed position and in the fixed position in the cylindrical body 60 by, for example, concavo-convex fitting structure or screwing.

Further, a holding recessed part 312 capable of holding part of a patient body is formed on an end surface on one side of the holding part 310. In this case, the holding recessed part 312 is open on an outer peripheral side of the holding part 310 and one end side, and is formed in a recessed portion surrounded by a pair of side surfaces 312a, a mounting surface 312b and a bottom surface 312c. One of the pair of side surfaces 312a is formed to be longer than the other, and the mounting surface 312b is tilted with respect to the pair of side surfaces 312a. Toes 15 of a leg 14 can be disposed in the holding recessed part 312 so as to be placed on the mounting surface 312b, whereby it is possible to keep a spot to be imaged (for example, knee joint or hip joint) of a patient at a given position.

That is, for example, in a case where CT imaging of a knee joint of a leg is performed, the knee joint of the leg 14 is easily disposed and kept in the state of standing still at a given position between the X-ray source 36 and the X-ray detector 37 by disposing the toes 15 in the holding recessed part 312. In this state, the X-ray source 36 and the X-ray detector 37 are rotated to perform X-ray CT imaging of the knee joint or the like. On this occasion, the cylindrical body 60 and the holding part 310 are relatively rotatable with respect to the support part 30, and thus the support part 310 can be rotated without rotating the holding part 310. Accordingly, it is possible to keep the holding state of the toes 15 while X-ray CT imaging is performed, and hence X-ray CT imaging can be performed even while the knee joint or the like to be imaged is caused to stand still at a given position, which suppresses a failure of X-ray CT imaging. In particular, positioning accuracy is required in local X-ray CT imaging where part of a patient is to be imaged, and thus the configuration described above is considered effective.

In an example shown in FIGS. 24 to 29, description is given of an example in which a holding part 410 as well as an extension part 430 are provided to a cylindrical body 460.

Figure 24:
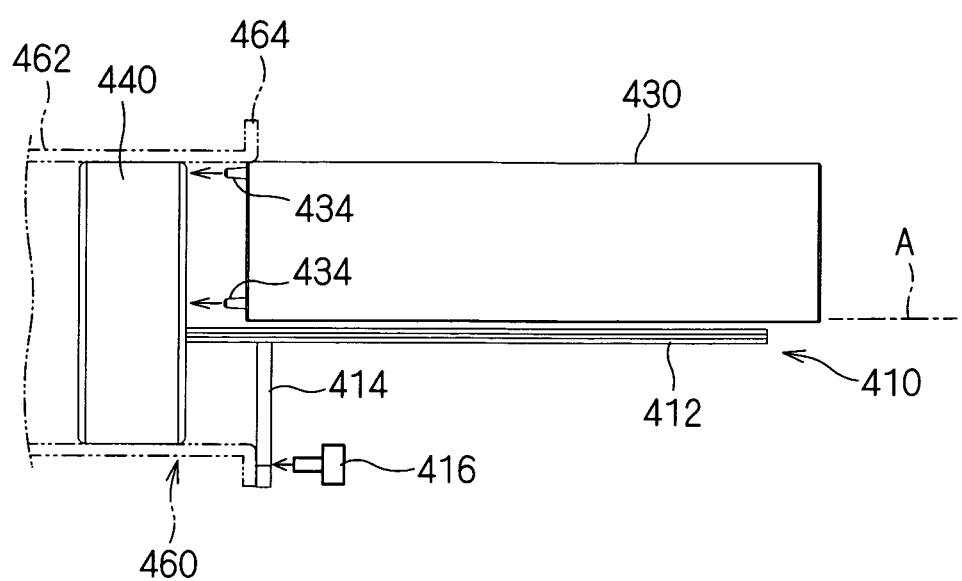
FIG. 24 is a side view of main parts according to a third modification of the first preferred embodiment, which shows an example in which the holding part as well as an extension part are provided in the cylindrical body.
Figure 25:
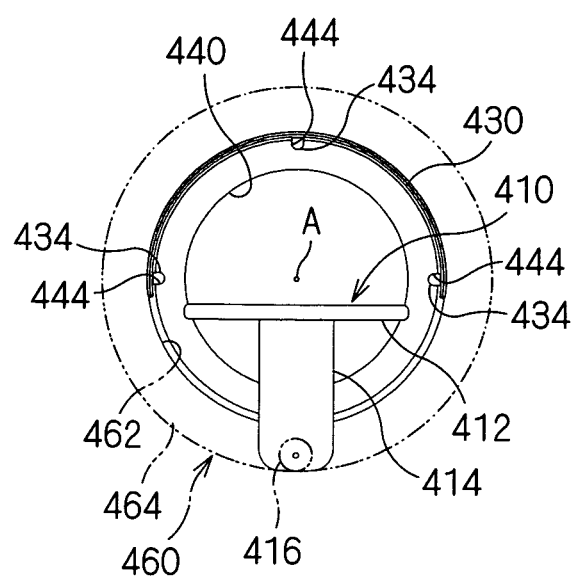
FIG. 25 is a front view showing the holding part and the extension part according to the third modification of the first preferred embodiment.
Figure 26:
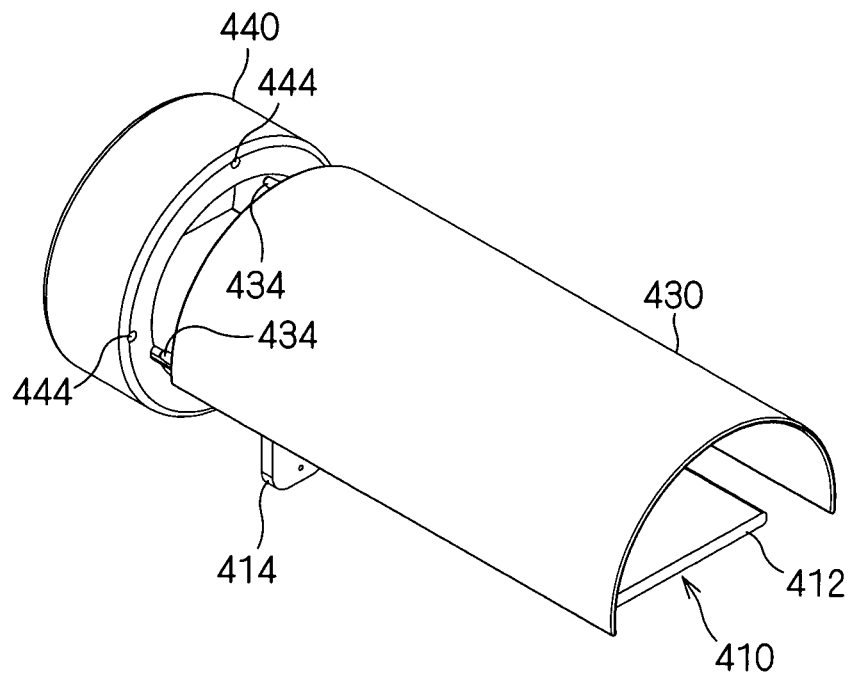
FIG. 26 is a perspective view showing the holding part and the extension part according to the third modification of the first preferred embodiment.
Figure 27:
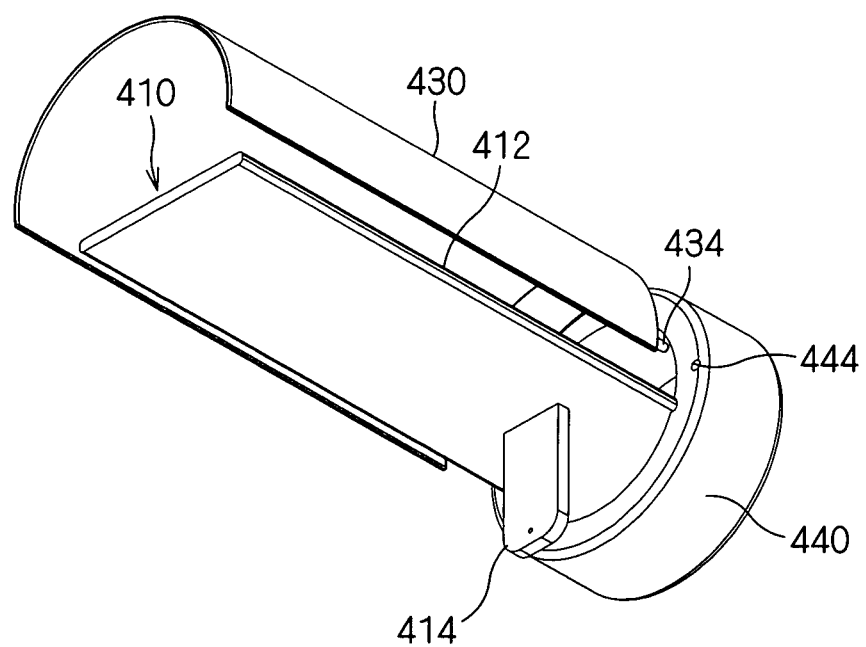
FIG. 27 is another perspective view showing the holding part and the extension part according to the third modification of the first preferred embodiment.
Figure 28:
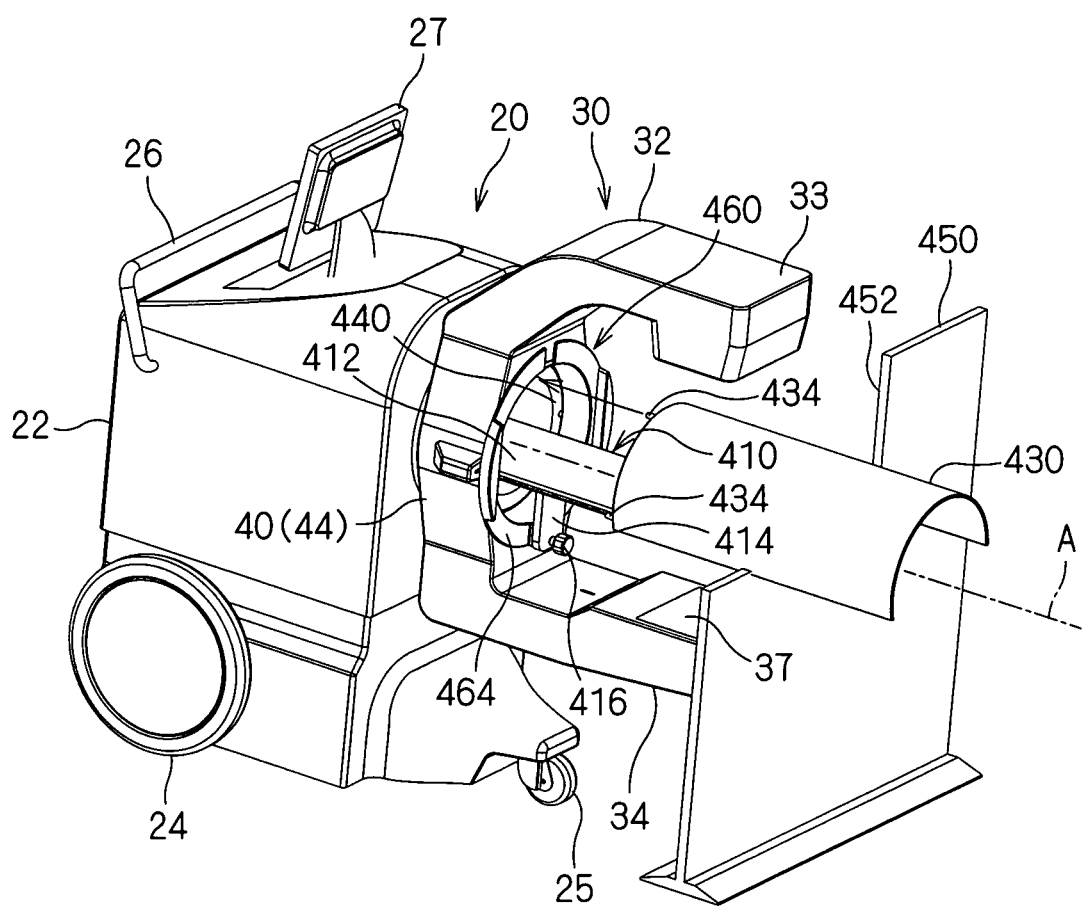
FIG. 28 is a perspective view showing a medical X-ray CT imaging apparatus provided with the holding part and the extension part according to the third modification of the first preferred embodiment.

The cylindrical body 460 is configured such that a flanged part 464 that extends toward an outside of the cylindrical body 460 in a radial direction is formed at an outer peripheral part of an opening of a cylindrical body main body part 462 having a similar configuration to that of the cylindrical body 60 of the first preferred embodiment (see FIGS. 24, 25 and 28).

The holding part 410 holds part of a patient body outside the cylindrical body 460 and, in this case; includes a plate-like part 412, a mounting piece 414 and a screw part 461.

The plate-like part 412 is formed in an approximately rectangular plate shape, and at least one end thereof has a width so as to be provided in the cylindrical body 460. In this case, the plate-like part 412 is formed to have approximately the same width in a longitudinal direction thereof.

The mounting piece 414 is formed into an elongated-plate-like piece provided on one principal surface (principal surface on a lower side in FIGS. 24, 25 and the like) of the plate-like part 412 approximately in a suspended manner. At a tip of the mounting piece 414, a screw insertion hole into which the screw part 416 can be inserted is formed, and a screw hole that enables the screw part 416 to be screwed with the flanged part 464 is formed. Note that a length dimension of the mounting piece 414 and a position of the screw hole are set so that the plate-like part 412 is disposed at a position lower than the rotation axis A.

Then, in the state where the plate-like part 412 is caused to be substantially horizontal and one end thereof is disposed in the cylindrical body 460, the screw part 416 is inserted into the screw insertion hole of the mounting piece 414 and also is screwed with the screw hole of the flanged part 464. Then, the mounting piece 414 is sandwiched between the flanged part 464 and a screw head of the screw part 416, whereby the holding part 410 can be detachably attached and fixed to the flanged part 464 in a given position.

The spot to be imaged that is placed on the plate-like part 412 is caused to be disposed on the rotation axis A.

The extension part 430 is provided, at an opening of the cylindrical body 460 that is open toward the space between the X-ray source 36 and the X-ray detector 37, so as to extend toward an inner side of a turning locus of the X-ray source 36 and the X-ray detector 37 around the rotation axis A.

More specifically, the extension part 430 is detachably attached to the cylindrical body 460 through a cylinder side attachment member 440 provided in the cylindrical body 460.

The extension part 430 has a shape obtained by partially cutting a bottomless cylindrical shape along its axial direction. A cross-section of the extension part 430 on a surface substantially orthogonal to the rotation axis A has an arc shape capable so as to be disposed in the cylindrical body 460, and an outer peripheral surface thereof forms an arc having approximately the same diameter as that of an inner peripheral surface of the cylindrical body 460. The cross-section of the cylindrical body 460 forms an arc shape larger than a half arc, and in a state where one end of the extension part 430 in an axial direction is disposed in the cylindrical body 460, both side parts of the extension part 430 in the circumferential direction are provided below exceeding a line in diameter direction of the cylindrical body 460. Accordingly, in the state where one end of the extension part 430 in the axial direction is disposed in the cylindrical body 460, an outer peripheral surface of the extension part 430 is in contact with the inner peripheral surface of the cylindrical body 460 in a range exceeding 180° around the rotation axis A, with the result that a position in which the other end of the extension part 430 in the axial direction extends from the opening of the cylindrical body 460 in a substantially horizontal position is held stably.

On one end surface of the extension part 430, pin-shaped fitting protrusions 434 are provided in a protruding manner. In this case, three fitting protrusions 434 are formed on one end surface of the extension part 430 at substantially equal intervals.

The cylinder side attachment member 440 is formed into a circular member so as to be disposed in the cylindrical body 460 in the state of being in contact with the inner peripheral surface of the cylindrical body 460 (see FIGS. 24, 25 and 28). The cylinder side attachment member 440 is preferably disposed so as not to relatively rotate with respect to the cylindrical body 460 by, for example, concavo-convex fitting structure or press fitting structure into the cylindrical body 460.

Fitting recessed parts 444 into which the fitting protrusions 434 can be fitted are formed on an outer surface of the cylinder side attachment member 440. In this case, three fitting recessed parts 444 are formed at positions corresponding to the three fitting protrusions 434.

Note that the cylinder side attachment member 440 may be a member formed integrally with the cylindrical body 460 and, in other words, the fitting recessed parts 444 may be formed in the cylindrical body 460 itself.

One end of the extension part 430 is disposed so as to be fitted into the cylindrical body 460, and the fitting protrusions 434 are fitted into the corresponding fitting recessed parts 444, whereby the extension part 430 is detachably attached to the cylindrical body 460. In this state, the other end of the extension part 430 that extends beyond the cylindrical body 460 extends in a substantially horizontal position so as to surround the rotation axis A at a position above the plate-like part 412 (see FIG. 28). In this attachment state, the extension part 430 preferably extends at least up to a position beyond the pair of arm parts 33 and 34. Note that the extension part 430 is pulled out toward the opening side of the cylindrical body 460, whereby the extension part 430 can be detached from the cylindrical body 460.

In a case where X-ray CT imaging is performed, a partition panel 450 that is approximately orthogonal to the rotation axis A is disposed at a position outside the tips of the arm parts 33 and 34. In the partition panel 450, an approximately L-shaped cutout 452 is formed so as to make the extension of the rotation axis A open. Note that a height of a horizontal side portion of the cutout 452 and elevational positions of the end surfaces on both sides of the extension part 430 in the circumferential direction and a lower surface of the plate-like part 412 of the holding part 410 may be caused to coincide with each other, and the end surfaces on both sides of the extension part 430 in the circumferential direction and the lower surface of the plate-like part 412 of the holding part 410 may be supported by the horizontal side portion of the cutout 452 in a mounted state, to thereby regulate the extension part 430, the cylindrical body 460, the holding part 410 and the like so as not to rotate.

Then, in the above-mentioned state, a stool or the like is placed outside the partition panel 450, and a patient sitting on the stool puts an arm between the plate-like part 412 and the extension part 430 though the cutout 452. On this occasion, fingers can be placed in the cylindrical body 460, and thus the arm is extended out so far toward the cylindrical body 460 that an upper arm portion and the like are placed between the X-ray source 36 and the X-ray detector 37. With the use of an inner space surrounded by the plate-like part 412 and the extension part 430, a spacer such as a resin that has a small X-ray absorption coefficient is put between the inner space and the arm so that the arm is fixed more reliably.

After that, in this state, the X-ray source 36 and the X-ray detector 37 are rotated around the rotation axis A, whereby X-ray CT imaging can be performed. In order to perform the X-ray CT imaging, the plate-like part 412 and the extension part 430 are formed of a material having a small X-ray absorption coefficient at least in a range in which X-rays are irradiated.

On this occasion, the cylindrical body 460 and the holding part 410 are relatively rotatable with respect to the support part 30, and thus it is possible to perform X-ray CT imaging by rotating the support part 30 without rotating the holding part 410. Accordingly, the holding state at the given position of the arm or the like can be maintained, whereby it is possible to perform X-ray CT imaging while causing, for example, the arm to be imaged to stand still at a given position, which suppresses a failure of X-ray CT imaging.

During imaging, the extension part 430 is interposed between the X-ray source 36 and the X-ray detector 37, more specifically, between the arm or the like to be imaged and the X-ray source 36. For this reason, the contact between the arm or the like to be imaged and the X-ray source 36 or the X-ray detector 37 is suppressed more reliably.

The extension part 430 is attached so as to be connected to and separated from the opening of the cylindrical body 460, and thus the extension part 430 can be attached/detached in accordance with the spot to be imaged. In a case where the extension part 430 becomes an obstacle, such as a case where a neck is imaged, imaging is performed while detaching the extension part 430. Alternatively, in a case where an elongated portion such as an arm and a leg is imaged, imaging can be performed while attaching the extension part 430. Accordingly, X-ray CT imaging of various spots can be performed by attaching/detaching the extension part 430 in accordance with a spot to be imaged.

Figure 29:
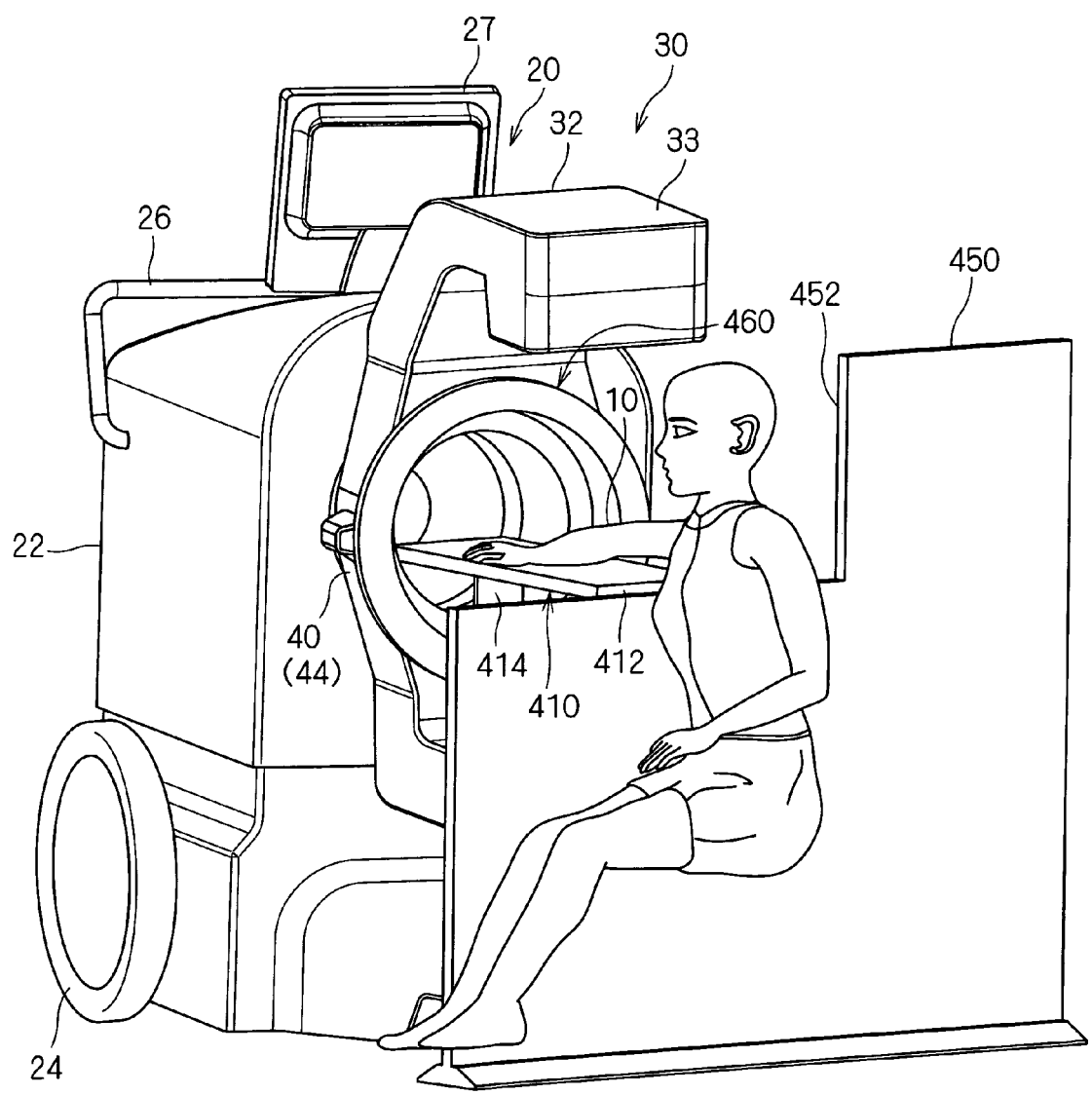
FIG. 29 is a perspective view showing a medical X-ray CT imaging apparatus provided with the holding part according to the third modification of the first preferred embodiment.
Figure 30:
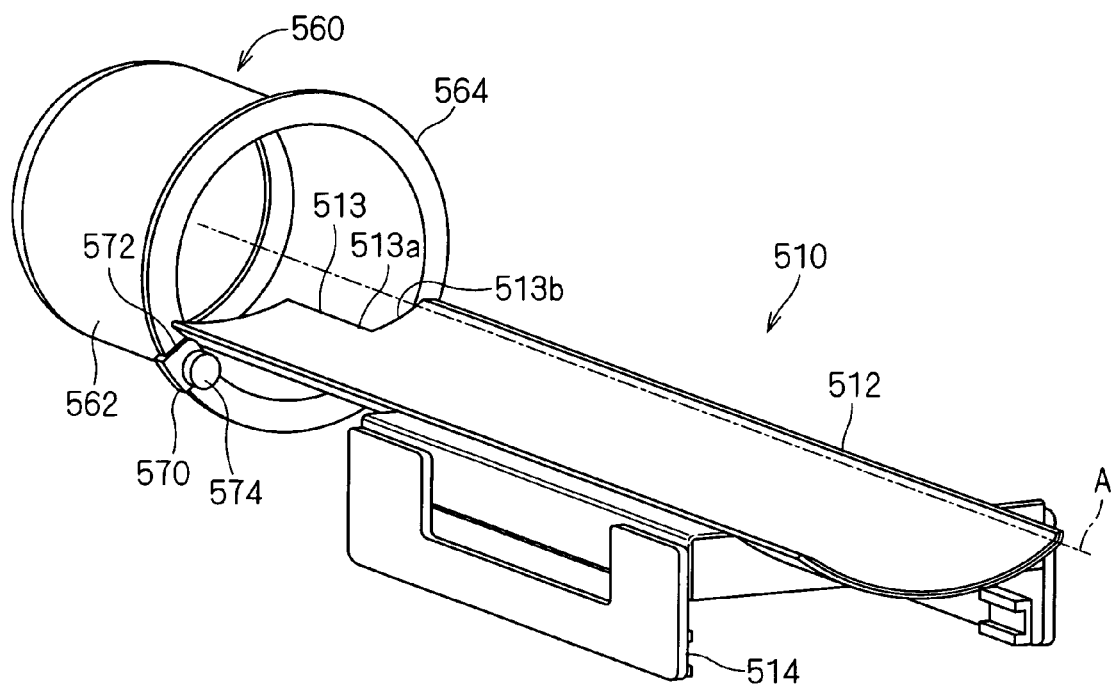
FIG. 30 is a perspective view showing, according to the third modification of the first preferred embodiment, an example in which a connecting and separating part for connecting a medical bed to the cylindrical body is provided.
Figure 31:
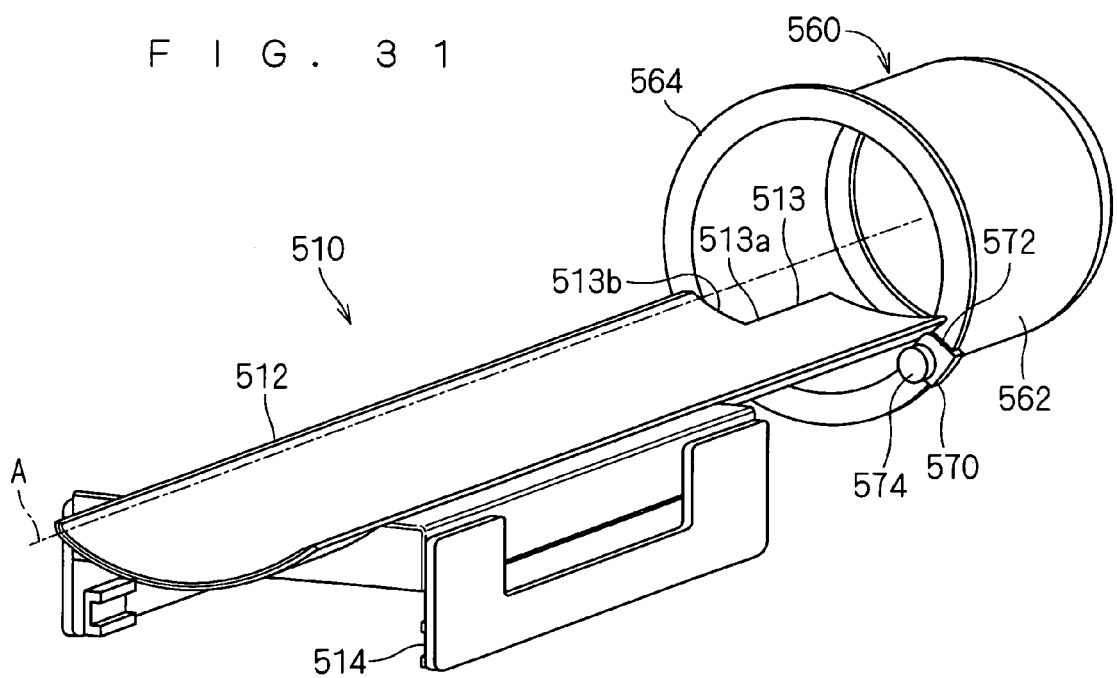
FIG. 31 is a perspective view showing the connecting and separating part and the medical bed according to the third modification of the first preferred embodiment.

Note that description above is given by way of an example in which the holding part 410 and the extension part 430 are provided, not necessarily limited thereto. For example, only the extension part 430 may be provided, or only the holding part 410 may be provided as shown in FIG. 29. That is, in FIG. 29, the arm 10 of a seated patient is caused to extend in a substantially horizontal position toward the apparatus 20 side and is placed on and supported by the plate-like part 412 of the holding part 410, to thereby perform X-ray CT imaging in this state.

In an example shown in FIGS. 30 to 37, description is given of an example for causing an external holding member located outside the medical X-ray CT imaging apparatus 20 to be connected to and separated from a cylindrical body 560. The description is given here assuming a case where the external holding member is a medical bed 510 that holds an entire patient body. Needless to say, in addition to a bed, the external holding member may be a member that holds part of a patient body, such as a support that supports an arm in a placed manner.

Figure 36:
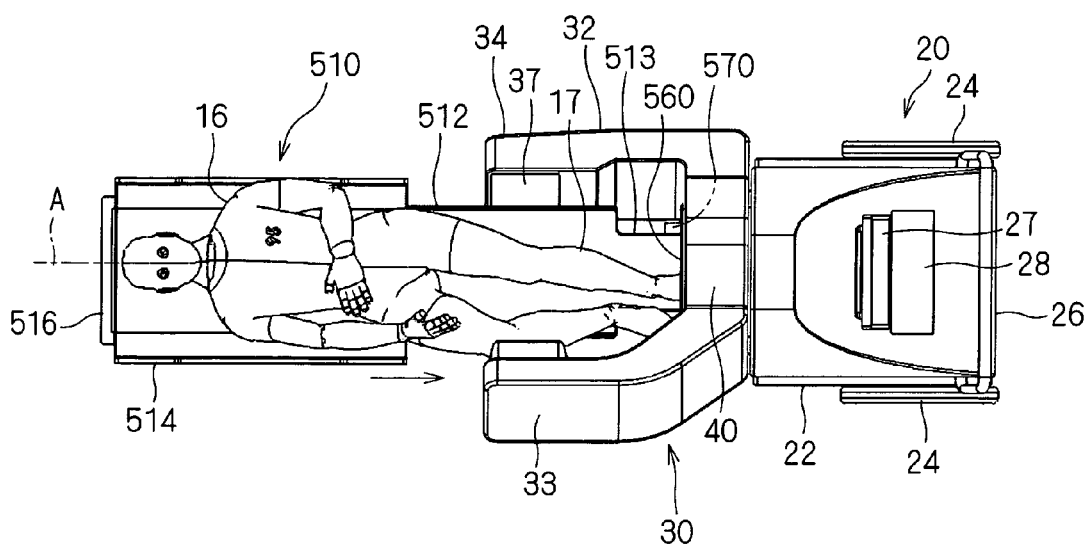
FIG. 36 is a front view showing an example of imaging using the connecting and separating part and the medical bed according to the third modification of the first preferred embodiment.
Figure 37:
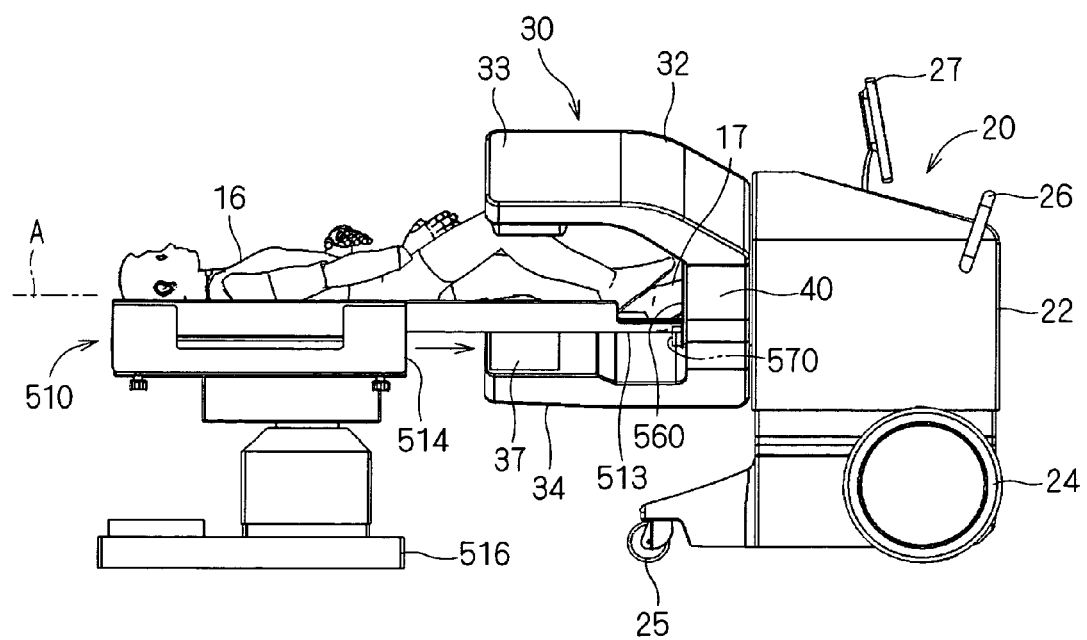
FIG. 37 is a side view showing the example of imaging using the connecting and separating part and the medical bed according to the third modification of the first preferred embodiment.

The medical bed 510 includes a bed main body part 512, an intermediate rack 514 and a lower base 516 (see FIGS. 36 and 37).

The bed main body part 512 is formed in an elongated plate shape that is recessed in an arc shape from both side parts toward a center part in a width direction. The bed main body part 512 is formed to have a width dimension and a length dimension so as to support an average human who is lying down. The bed main body part 512 is configured such that horizontal part, which is related to a body axis of a patient or the like to be placed, of one end side portion 513 thereof is cut out in an approximately L shape to form a first side portion 513a extending along the longitudinal direction of the bed main body part 512 and a second side portion 513b extending along a width direction thereof.

The one end side portion 513 can be disposed in the cylindrical body 560 while causing the second side portion 513b to abut against an opening portion of the cylindrical body 560.

The bed main body part 512 is supported in a substantially horizontal position at the elevational position corresponding to the cylindrical body 560 by the intermediate rack 514 and the lower base 516. The one end side portion 513 is fixed to the intermediate rack 514 so as to extend beyond the intermediate rack 514.

The cylindrical body 560 is configured such that a flanged part 564 extending toward an outside of the cylindrical body 560 in the radial direction is formed at an outer peripheral part of an opening of a cylindrical body main body portion 562 that has a similar configuration to that of the cylindrical body 60 according to the first preferred embodiment.

Figure 33:
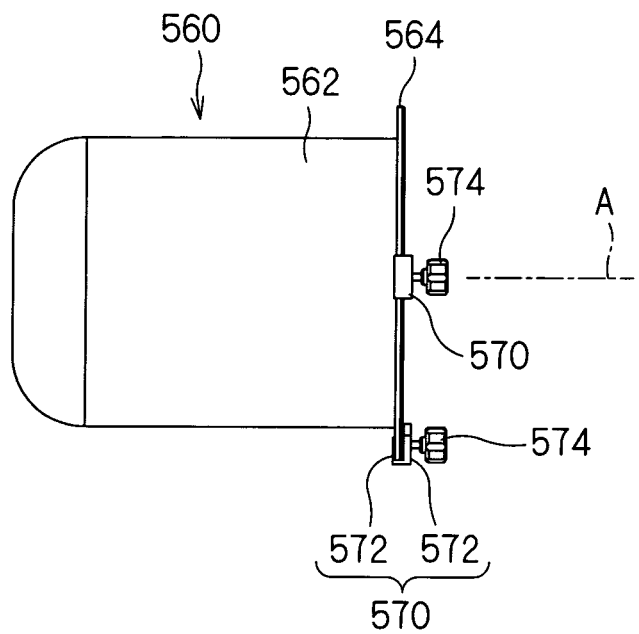
FIG. 33 is a side view showing the cylindrical body provided with the connecting and separating part according to the third modification of the first preferred embodiment.
Figure 34:
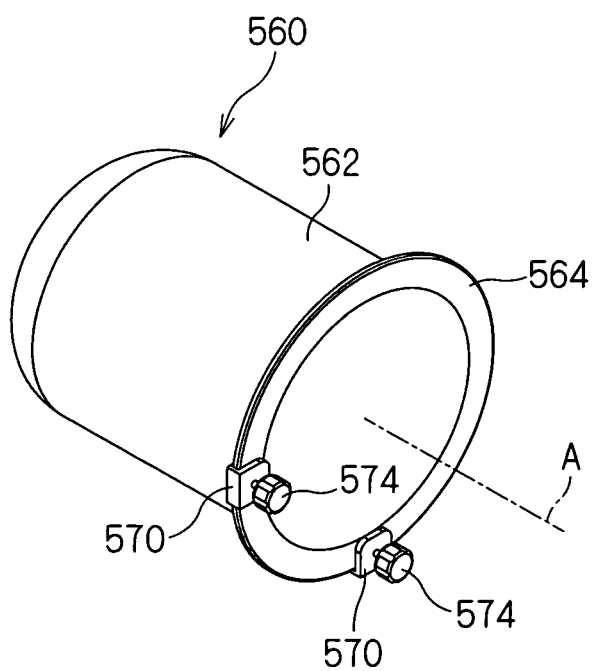
FIG. 34 is a perspective view showing the cylindrical body provided with the connecting and separating part according to the third modification of the first preferred embodiment.
Figure 35:
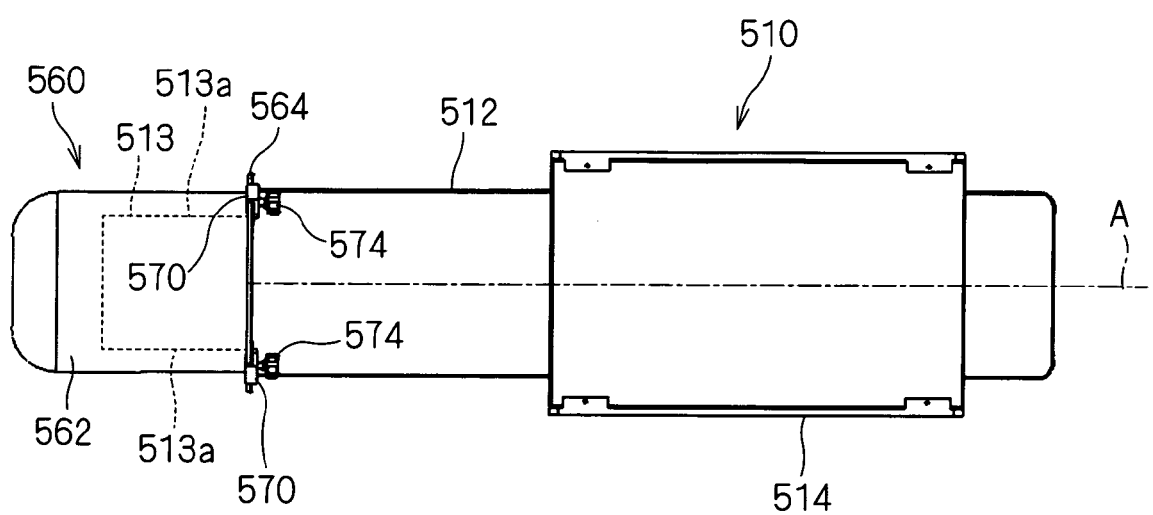
FIG. 35 is a bottom view showing the connecting and separating part and the medical bed according to the third modification of the first preferred embodiment.

A connecting and separating part 570 is configured such that a pair of sandwiching sides 572 are arranged so as to be opposed to each other with an interval therebetween (see FIGS. 33 and 34). The interval at which the flanged part 564 can be disposed is provided between the pair of sandwiching sides 572. In addition, a fixing screw parts 574 are disposed to one of the pair of sandwiching sides 572 in a screwed state. The fixing screw parts 574 are fastened in the state where the connecting and separating parts 570 are disposed at a desired position in the circumferential direction of the flanged part 564 such that the flanged part 564 is sandwiched between the pair of sandwiching sides 572. Accordingly, the flanged part 564 is sandwiched between tips of the fixing screw parts 574 and the other of the pair of sandwiching parts 572, whereby the connecting and separating part 570 is fixed at a desired position of the flanged part 564. In this case, two connecting and separating parts 570 are provided. Two connecting and separating parts 570 are attached and fixed to the flanged part 564 at positions so as to abut against the second side portion 513b from therebelow in a state in which the one end side portion 513 of the bed main body part 512 is disposed in the cylindrical body 560 (see FIG. 32).

The one end side portion 513 of the bed main body part 512 is disposed in the cylindrical body 560, and lower surface portions of the second side portions 513b are caused to abut against the connecting and separating part 570, whereby the bed main body part 512 is detachably connected to the cylindrical body 560. In this state, the lower surfaces of the second side portions 513b of the bed main body part 512 that is held in a predetermined horizontal position abut against the connecting and separating part 570. For this reason, rotation of the cylindrical body 560 is regulated more reliably. Here, the connection between the cylindrical body and the external holding member refers to a fact that the cylindrical body and the external holding member are integrated in the state where the rotation of the cylindrical body with respect to the external holding member is regulated. On the other hand, the separation of the cylindrical body and the external holding member refers to a fact that the cylindrical body and the external holding member are apart from each other in the state where the regulation of rotation of the cylindrical body to the external holding member is released.

For example, in a case of imaging a knee joint of a patient as a spot to be imaged, operation is made as shown in FIGS. 36 and 37. That is, a patient 16 is laid down on the bed main body part 512 such that a leg 17 is disposed in the one end side portion 513, whereby one leg to be imaged is disposed on the rotation axis A while the other leg not to be imaged is bent to be positioned in a place other than the X-ray irradiated region. Then, at least one of the medical bed 510 and the medical X-ray CT imaging apparatus 20 is moved so that the one end side portion 513 of the bed main body part 512 is disposed in the cylindrical body 560 and that the lower surfaces of the second side portions 513b are caused to abut against the connecting and separating part 570. In this state, the X-ray source 36 and the X-ray detector 37 are rotated around the rotation axis A, which enables X-ray CT imaging.

As a result, it is possible to perform X-ray CT imaging in the state where the leg or the like of the patient to be imaged is caused to stand still at a given position, which suppresses, for example, a failure of X-ray CT imaging.

Moreover, when the bed main body 512 and the medical X-ray CT imaging apparatus 20 are moved to be close to or apart from each other, the connection and separation described above are enabled, which is convenient for a user. Further, a burden is significantly reduced for a patient who has difficulty in moving though he/she requires X-ray CT imaging.

The respective configurations according to this third modification are advantageous in that they can be achieved relatively with ease and with a simple configuration by, for example, exchanging cylindrical bodies or adding a holding part or the like in the medical X-ray CT imaging apparatus 20 described in the first preferred embodiment.

Second Preferred Embodiment

A medical X-ray CT imaging apparatus according to the second preferred embodiment is described. Note that in the description of this preferred embodiment, similar elements to those described in the first preferred embodiment are denoted by like reference symbols, and description thereof is omitted. FIGS. 38 to 43 are views showing main parts of the medical X-ray CT imaging apparatus according to the second preferred embodiment. In the medical X-ray CT imaging apparatus, the cylindrical body 660 is attached to the base.

That is, in the base corresponding to the base 22 according to the first preferred embodiment, a drive part mounting plate 638 is supported such that a given position or position thereof can be changed. A support shaft part 610 is mounted onto and fixed to the drive part mounting plate 638 by screwing or the like, and a rotary drive part 650 such as a motor is mounted and fixed next to the support shaft part 610 through a bracket or the like.

One end of the support shaft part 610 is formed in a substantially cylindrical shape, and the support part 30 is rotatably supported with respect to the support shaft part 610 through bearing parts 612 provided on an outer periphery thereof. Further, on an end surface of the one end of the support shaft part 610, the cylindrical body 660 is supported so as not to rotate with respect to the support shaft part 610.

More specifically, bearings 612 (see FIG. 43) are provided on the outer periphery on one end of the support shaft part 610, in each of which an outer ring member 612a and an inner ring member 612b are connected so as to relatively rotate through a rolling element such as a ball. The inner ring member 612b is attached and fixed to the one end of the support shaft part 610 through a screw or the like, whereas the outer ring member 612a is attached and fixed to a bottom of the inner side rotation support part 42 of the support part 30 through a screw or the like. As a result, the support part 30 is supported so as to relatively rotate at a fixed position with respect to the support shaft part 610.

Needless to say, as in the second modification of the first preferred embodiment described above, various types of bearings such as a journal bearing may be appropriately used as the bearing in this case. Alternatively, there may be used a sliding bearing or a rolling bearing and, in the case of the rolling bearing, a ball bearing or a roller bearing may be used.

Figure 38:
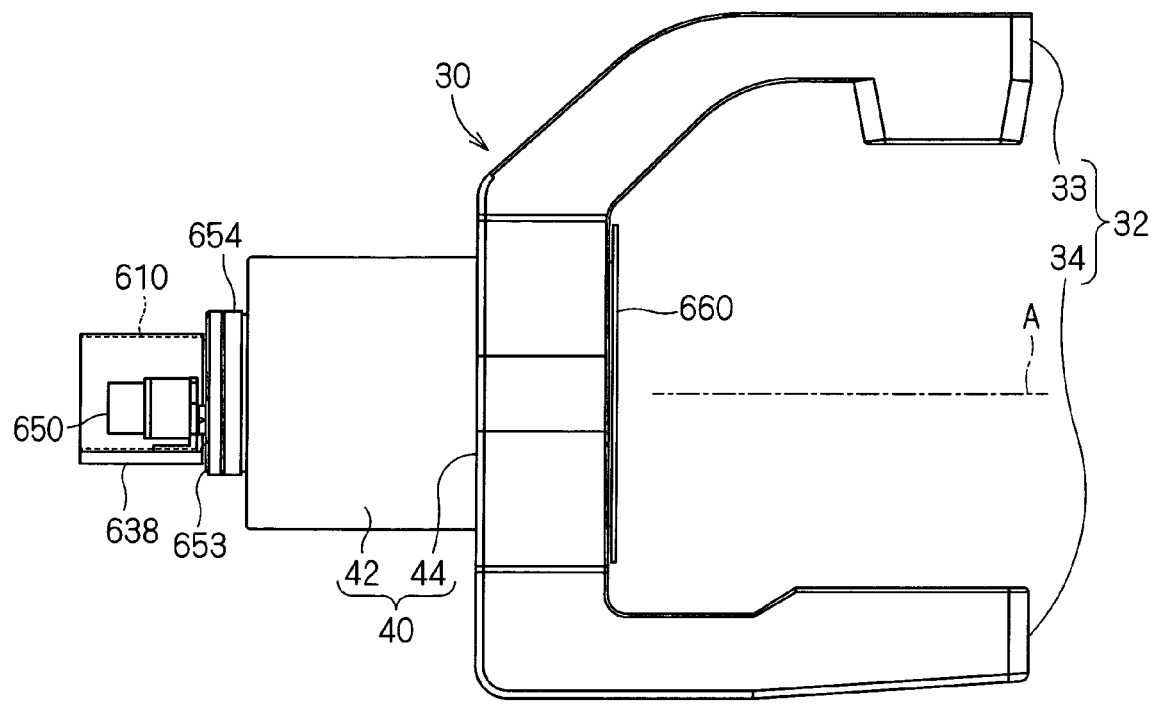
FIG. 38 is a side view showing a support part and a rotary drive part of a medical X-ray CT imaging apparatus according to a second preferred embodiment.
Figure 39:
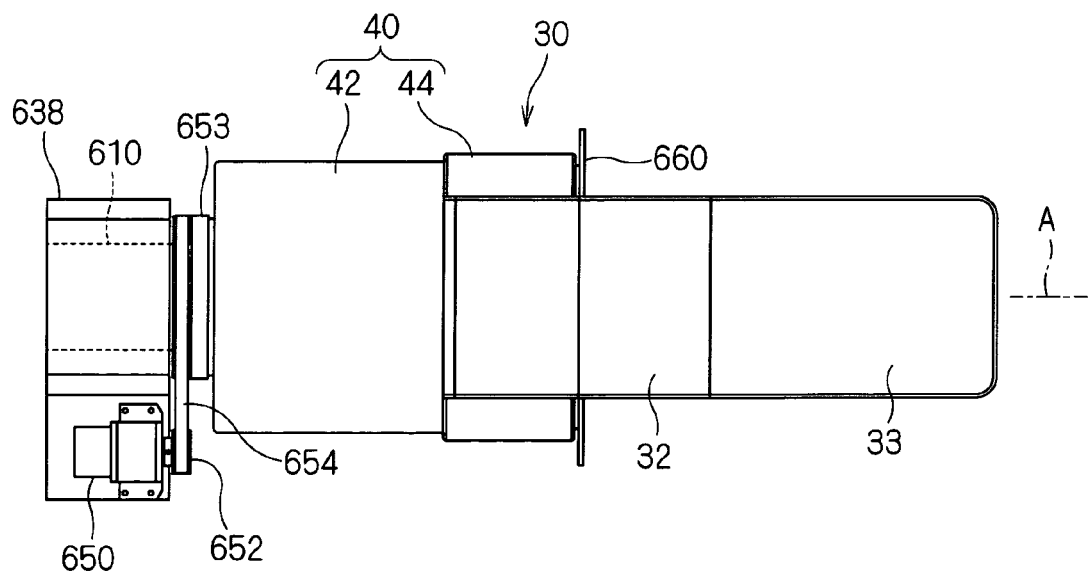
FIG. 39 is a plan view showing the support part and the rotary drive part of the medical X-ray CT imaging apparatus according to the second preferred embodiment.
Figure 41:
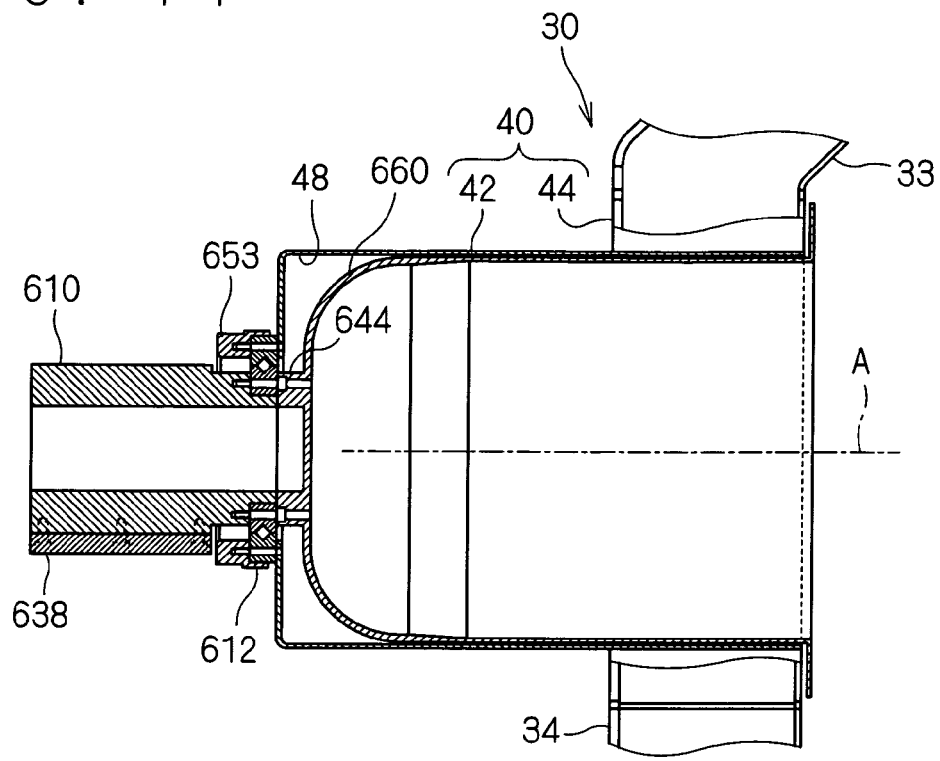
FIG. 41 is a cross-sectional view showing the support part and a cylindrical body of the medical X-ray CT imaging apparatus according to the second preferred embodiment.
Figure 42:
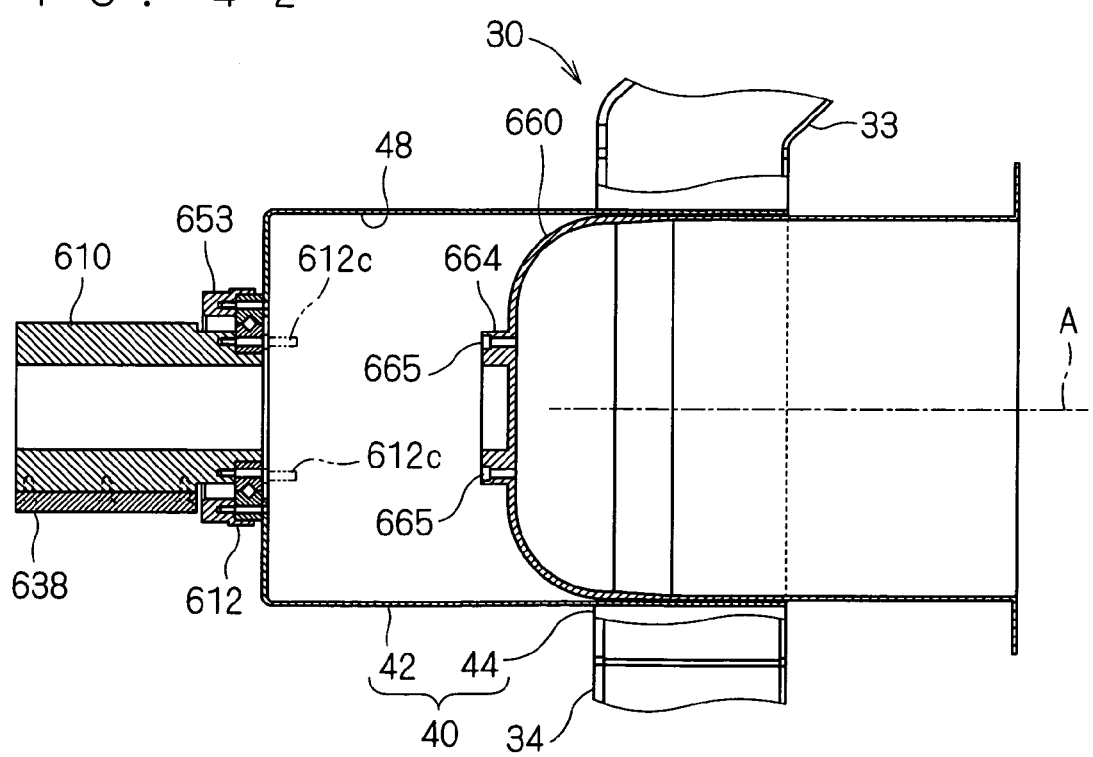
FIG. 42 is a cross-sectional view showing a state in which the cylindrical body is detached in FIG. 41.
Figure 43:
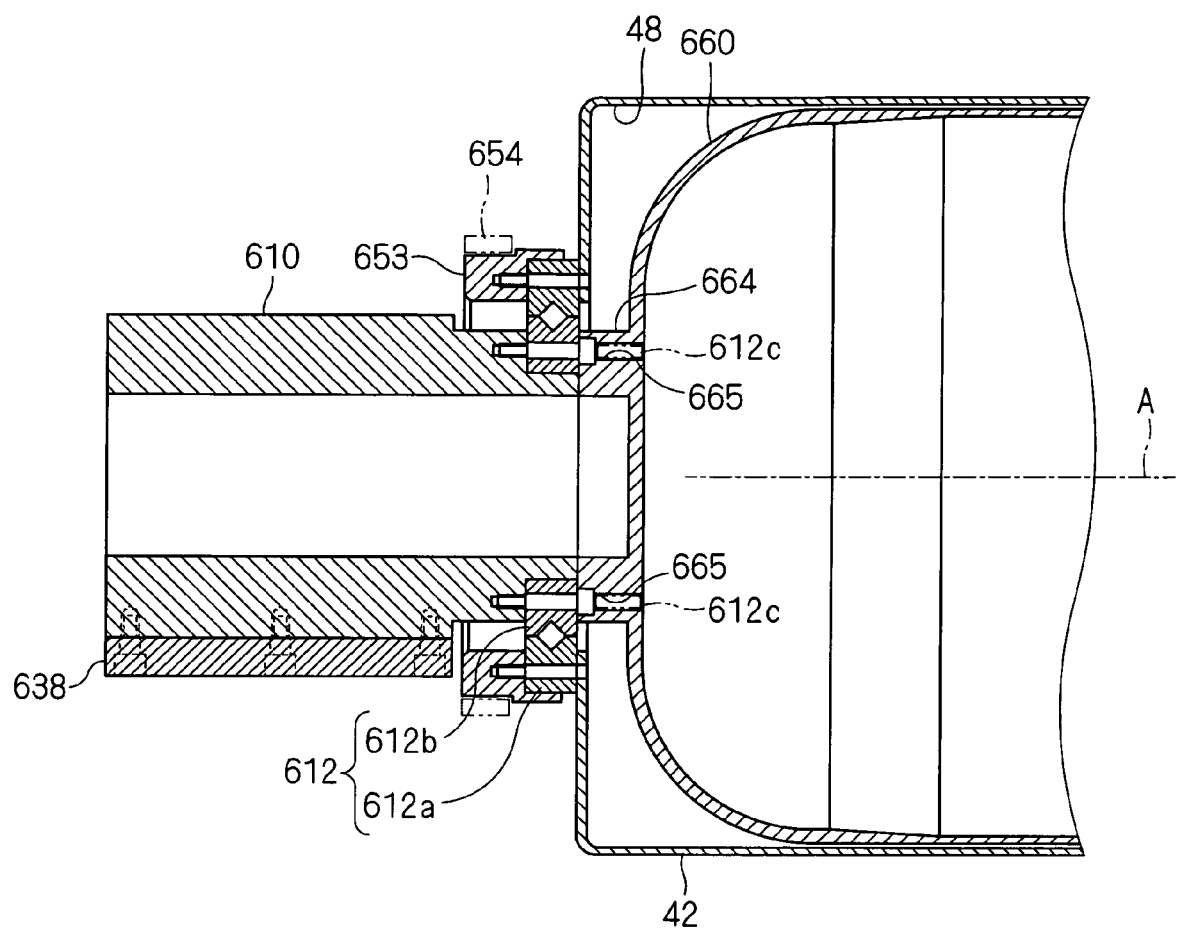
FIG. 43 is a partial cross-sectional view of FIG. 41.

Further, a drive belt 654 that has no end and a circular shape is wound around a pulley body 652 mounted onto a rotary shaft part of the rotary drive part 650 and a pulley body 653 provided on the outer periphery of the outer ring member 612a (see FIGS. 38, 39 and 40). A rotary driving force of the rotary drive part 650 is transmitted to the rotation support part 40 through the drive belt 654, and accordingly the support part 30 is rotatively driven.

Further, a circular mounting part 664 is provided on a bottom surface of the cylindrical body 660 corresponding to the cylindrical body 60 according to the first preferred embodiment. The circular mounting part 664 is a circular member formed at a position corresponding to the inner ring member 612b, and is formed so as to have surface contact with an outer surface of the inner ring member 612b through a circular surface. In addition, a pin-like projection 612c is formed on the outer surface of the inner ring member 612b (see FIGS. 42 and 43). In this case, the projection 612c is formed by forming a head part of a screw for fixing the inner ring member 612b to the support shaft part 610 in a pin shape, and multiple projections 612c are provided along a circular shape at intervals. At portions on the side of the circular mounting part 664, which is in contact with the inner ring member 612b, multiple fitting hole parts 665 into which the projections 612c can be inserted are formed.

The respective projections 612c are fitted into the fitting hole parts 665 when the cylindrical body 660 is fitted into the cavity 48 of the rotation support part 40 to a deep position, whereby the cylindrical body 660 is mounted onto the base 22 at a fixed position so as not to rotate with respect to the base 22 through the inner ring member 612b, the support shaft part 610 and the like. In addition, the fitting of each projection 612c into each fitting hole part 665 is released when the cylindrical body 660 is pulled out from the cavity 48 of the rotation support part 40 toward the opening side, whereby the cylindrical body 660 can be detached from the base 22.

According to the above-mentioned second preferred embodiment, the cylindrical body 660 is mounted onto the base 22 at a fixed position so as not to relatively rotate with respect to the base 22, and hence it is possible to prevent the cylindrical body 660 from rotating with more reliably even when the support part 30 is rotated for performing X-ray CT imaging. Therefore, X-ray CT imaging can be performed in a state where the spot to be imaged is kept to stand still with more reliability, which suppresses a failure of X-ray CT imaging with more reliability.

First Modification

Figure 44:
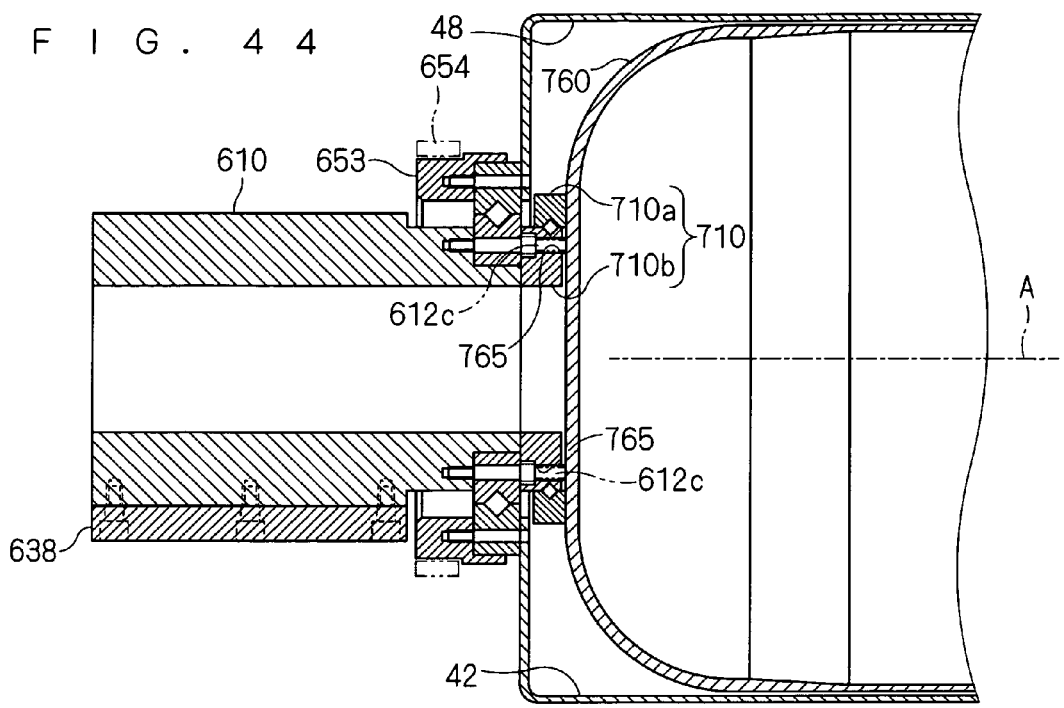
FIG. 44 is a partial cross-sectional view showing a support part and a cylindrical body according to a first modification of the second preferred embodiment.

A first modification according to the second preferred embodiment is described. In the description of this modification, for example, similar elements to those described in the second preferred embodiment described above are denoted by like reference symbols, and description thereof is omitted. FIG. 44 is a view showing main parts of a medical X-ray CT imaging apparatus according to this modification.

In this modification, a cylindrical body 760 corresponding to the cylindrical body 60 according to the first preferred embodiment is attached to the support shaft 610 through bearing parts 710, and is mounted onto the base 22 at a fixed position so as to rotate with respect to the base 22.

More specifically, the bearing parts 710 are provided between one end of the support shaft part 610 and a bottom of the cylindrical body 760. The bearing part 710 is configured such that an outer ring member 710a and an inner ring member 710b are connected so as to relatively rotate through a rolling element such as a ball. In the inner ring member 710b, a fitting hole part 765 that is similar to the fitting hole part 665 is formed so that each projection 612c is detachably fitted into the fitting hole part 765. Note that the inner ring member 710b is not fixed to the cylindrical body 760. In addition, the outer ring member 710a is attached and fixed to the bottom of the cylindrical body 760 through a screw or the like.

Needless to say, as in the second modification of the first preferred embodiment described above, various types of bearings such as a journal bearing may be appropriately used as the bearing in this case. Alternatively, there may be used a sliding bearing or a rolling bearing and, in the case of the rolling bearing, a ball bearing or a roller bearing may be used.

When the cylindrical body 760 is fitted into the cavity 48 of the rotation support part 40 to a deep position, each projection 612c is detachably fitted into the fitting hole part 765, whereby the inner ring member 710b of the bearing part 710 is attached and fixed to the support shaft part 610 at a fixed position so as not to rotate with respect to the support shaft part 610. Then, the outer ring member 710a relatively rotates with respect to the inner ring member 710b, whereby the cylindrical body 760 can relatively rotate with respect to the support shaft part 610. As described above, the cylindrical body 760 is attached to the support shaft part 610, that is, to the base at a fixed position so as to relatively rotate with respect to the base.

According to this modification, it is possible to adjust the rotation of the cylindrical body 760 around the rotation axis A, whereby the rotation of the cylindrical body 760 can be adjusted in accordance with a state in the vicinity of the spot to be imaged that is disposed in the cylindrical body 760. For example, in a case where the holding part 310 is disposed in the cylindrical body 760, the cylindrical body 760 can be rotated such that a patient is in a comfortable position without feeling any pain in accordance with, for example, a position of part (that is, toe) of the patient held by the holding part 310.

Second Modification

Figure 45:
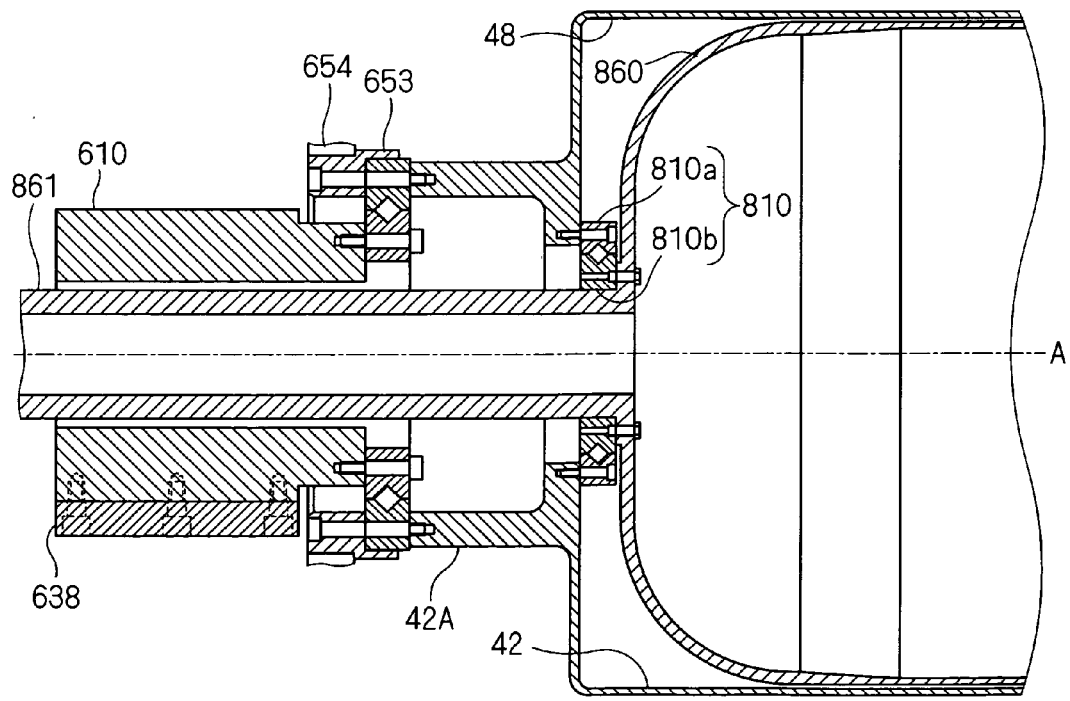
FIG. 45 is a partial cross-sectional view showing a support part and a cylindrical body according to a second modification of the second preferred embodiment.

A second modification according to the second preferred embodiment is described. In the description of this modification, for example, similar elements to those described in the second preferred embodiment described above are denoted by like reference symbols, and description thereof is omitted. FIG. 45 is a view showing main parts of a medical X-ray CT imaging apparatus according to this modification.

In this modification, a cylindrical body 860 corresponding to the cylindrical body 60 according to the first preferred embodiment is attached to the inner side rotation support part 42 through bearing parts 810 and is mounted onto the base 22 at a fixed position with respect to the base 22.

More specifically, the bearing parts 810 are provided between an inner surface bottom of the inner side rotation support part 42 and a bottom of the cylindrical body 860. The bearing part 810 is configured such that an outer ring member 810a and an inner ring member 810b are connected so as to relatively rotate through a rolling element such as a ball. The outer ring member 810a is attached and fixed to the inner surface bottom of the inner side rotation support part 42 through a screw or the like. On the other hand, the inner ring member 810b is attached and fixed to the bottom of the cylindrical body 860 with a screw or the like.

Needless to say, as in the second modification of the first preferred embodiment described above, various types of bearings such as a journal bearing may be appropriately used as the bearing in this case. Alternatively, there may be used a sliding bearing or a rolling bearing and, in the case of the rolling bearing, a ball bearing or a roller bearing may be used.

Further, a fix and support part 861 is extended from the bottom of the cylindrical body 860 toward the base 22, and when the cylindrical body 860 is fitted into the cavity 48 of the rotation support part 40 to a deep position, the fix and support part 861 is inserted into the rotation support part 40 and the support shaft part 610. At the same time, the end of the fix and support part 861 on the base side is fixed to the base 22 so as not to rotate with respect thereto. A cylindrical part 42A is extended to the bottom of the inner side rotation support part 42 with the direction same as the longitudinal direction of the fix and support part 861 being an axial direction, and bearings are interposed between the support shaft part 610 and the cylindrical body 42A so that the cylindrical part 42A relatively rotates with respect to the support shaft part 610.

As described above, the inner ring member 810b relatively rotates with respect to the outer ring member 810a, and thus the cylindrical body 860 is not capable of relatively rotating at a fixed position with respect to the support shaft part 610 even while the rotation support part 40 is rotating. As the configuration for attaching the fix and support part 861 to the base 22 so as not to relatively rotate with respect thereto, for example, the following configuration may be used, where a convex part is formed on any one of the fix and support part 861 side and the base 22 side, and a concave part is formed on the other side thereof, whereby both parts are fitted into each other in a concavo-convex shape (see mounting structure of the cylindrical body 660 of FIGS. 41 to 43). In particular, it is possible to adjust a mounting angle of the cylindrical body 860 to the base 22 around the rotation axis A by forming multiple convex parts at equal intervals around the rotation axis A and forming multiple concave parts at equal intervals around the rotation axis A.

According to this modification, an interval is provided between the support shaft part 610 and the bearing part 810 and, with the use of the interval, a cable including collective signal lines extending from the X-ray source 36 and the X-ray detector 37 is wound around the rotation support part 40, whereby it is possible to rotate the cable and the rotation support part 40 at the same time. Accordingly, disconnection of the signal lines and the like can be prevented with a simple configuration. Note that also in this modification, it is possible to adjust the rotation of the cylindrical body 860 around the rotation axis A before the end of the fix and support part 861 on the base side is fixed to the base 22. Accordingly, it is possible to adjust the rotation of the cylindrical body 860 in accordance with a state in the vicinity of the spot to be imaged that is disposed in the cylindrical body 860. For example, in a case where the holding part 310 is disposed in the cylindrical body 860, it is possible to rotate the cylindrical body 860 in accordance with a position or the like of part (that is, toe) of a patient held by the holding part 310 such that the patient is in a comfortable position without feeling any pain, which reduces a burden on the patient.

Common Modification

Note that the descriptions of the respective preferred embodiments and modifications are in all aspects illustrative and the present invention is not limited thereto.

For example, in the preferred embodiments, the cavity 48 is provided in the rotation support part 40, which is not necessarily required. For example, in a case where the rotary drive part 50 is omitted and a bearing, a rotary drive mechanism and the like are provided around an inner side rotation support part, a cavity may be formed in a base so as to be continuous with the cavity formed in the rotation support part. In this case, the cavity may be configured to be open toward both sides. Alternatively, for example, in a case where a rotary support part comprises ring-shaped bearings and one principal surface of a base is exposed in the space surrounded by the bearings so as to directly face the space between an X-ray source and an X-ray detector, a cavity may be provided in the base. Further, the cavity 48 is not necessarily required to have a round shape, and may have a polygonal shape or a shape corresponding to a shape of part of a patient body that is held in X-ray CT imaging. Further, there is conceivable a medical X-ray CT imaging apparatus having the configuration in which the cavity 48 is not provided in the rotation support part 40, the rotation support part 40 is provided within the base 22, and the tip of the support arm part 32 projects from the base 22. In this case, the cavity 48 is provided only on the base 22 side. Needless to say, the cavity 48 is provided so as to form the space between the X-ray source 36 and the X-ray detector 37 around the rotation axis.

The cylindrical body is not required to be a bottomed cylinder. For example, it may have a shape in which openings are provided on both sides in the axial direction, or may have a polygonal cylindrical shape.

While the description above is given by way of an example in which X-ray CT imaging is performed, simple X-ray imaging may be performed (simple transmission image may be obtained) without causing the X-ray source 36 and the X-ray detector 37 to rotate.

The respective configurations descried in the preferred embodiments and modifications can be appropriately combined with each other unless they are inconsistent with each other. For example, in the second preferred embodiment, the moving mechanism part 210 descried in the second modification of the first preferred embodiment may be incorporated, or the holding part or the like described in the third modification of the first preferred embodiment may be incorporated.

What is claimed is:

1. A medical X-ray CT imaging apparatus performing CT imaging of a part of a patient, the apparatus comprising:
    a base;
    a support part including:
        a support arm part supporting an X-ray source generating an X-ray cone beam and an X-ray detector so as to be opposed to each other; and
        a rotation support part supporting said support arm part in a rotatable manner with respect to said base so that said X-ray source and said X-ray detector rotate about a rotation axis along a horizontal direction; and
    a rotary drive part rotatively driving said support part, wherein:
    said support part includes a pair of arm parts, said X-ray source is mounted onto one of said pair of arm parts and said X-ray detector is mounted onto the other one of said pair of arm parts,
    said pair of arm parts is supported, outside of said base, with an interval for disposing a part of a patient to be imaged between said X-ray source and said X-ray detector such that said pair of arm parts extend from said rotation support part toward outside in a cantilevered manner,
    said rotation support part transmits a rotational force of said rotary drive part to said support arm part,
    said rotation support part includes a cavity around a rotation axis;
    a cylindrical body provided within said cavity in a rotatable state with respect to said support part so as to be rotatable about said rotation axis with respect to said rotation support part or to be fixed to said base, the cylindrical body being open to at least a space between said X-ray source and said X-ray detector, and
    a space formed inside said cylindrical body is located at a position displaced from an imaged region between said X-ray source and said X-ray detector.

2. The medical X-ray CT imaging apparatus according to claim 1, wherein said cylindrical body is formed in a cylindrical shape with said rotation axis being a center axis, and is rotatably held by the rotation support part through a bearing.

3. The medical X-ray CT imaging apparatus according to claim 1, wherein said cylindrical body is formed in a cylindrical shape with said rotation axis being a center, and is mounted onto said base.

4. The medical X-ray CT imaging apparatus according to claim 3, wherein said cylindrical body is mounted onto said base so as not to perform relative rotation around said rotation axis.

5. The medical X-ray CT imaging apparatus according to claim 3, wherein said cylindrical body is mounted onto said base in a rotationally adjustable manner around said rotation axis.

6. The medical X-ray CT imaging apparatus according to claim 1, further comprising a two-axially moving mechanism part enabling said support part to move along two axial directions, the two axial directions being orthogonal to said rotation axis and being orthogonal to each other.

7. The medical X-ray CT imaging apparatus according to claim 1, further comprising a rotation axis direction moving mechanism part enabling said support part to move along a rotation axis direction.

8. The medical X-ray CT imaging apparatus according to claim 1, further comprising:
 a Y direction moving mechanism part moving said support part in a Y direction along said rotation axis direction;
 a Z direction moving mechanism part moving said support part in a Z direction along a vertical direction; and
 an X direction moving mechanism part moving said support part in an X direction orthogonal to said Y direction and said Z direction,
 wherein said Z direction moving mechanism part moves said Y direction moving mechanism part and said X direction moving mechanism part in said Z direction.

9. The medical X-ray CT imaging apparatus according to claim 1, wherein said cylindrical body includes a holding part provided for holding a spot to be imaged of the patient at a given position.

10. The medical X-ray CT imaging apparatus according to claim 1, further comprising an X-ray regulating part regulating an irradiated region of the X-ray cone beam from said X-ray source, to thereby enable local CT imaging.

11. The medical X-ray CT imaging apparatus according to claim 1, wherein at least one of said support part and said cylindrical body is provided with a positioning light irradiation part irradiating light for positioning.

12. The medical X-ray CT imaging apparatus according to claim 1, wherein said cylindrical body is provided with a connecting and separating part enabling an external holding member to be connected thereto and separated therefrom, the external holding member g provided for holding a spot to be imaged at a given position.

13. The medical X-ray CT imaging apparatus according to claim 1, wherein said cylindrical body is formed in a bottomed cylindrical shape.

14. The medical X-ray CT imaging apparatus according to claim 1, wherein an opening of said cylindrical body is provided with an extension part extending to an inside of a turning locus of said X-ray source and said X-ray detector around said rotation axis, the opening being open toward the space between said X-ray source and said X-ray detector.

15. The medical X-ray CT imaging apparatus according to claim 14, wherein said extension part is attached to said opening so as to be connected thereto and separated therefrom.

16. The medical X-ray CT imaging apparatus according to claim 1, wherein said base includes a wheel capable of rolling on a floor.

17. The medical X-ray CT imaging apparatus according to claim 1, wherein:
 said X-ray source is disposed during rotation of said support part so that:
  when viewed from said rotation axis direction, a side portion on one side of an irradiated region of said X-ray cone beam inevitably passes through a periphery of an imaged region and a side portion on the other side thereof passes through an inner side than the periphery of said imaged region; and
  when viewed from a rotation axis direction, said X-ray cone beam irradiates a region of a half or more of an entire region of said imaged region that is less than the entire region of said imaged region; and
 said support part is configured so as to turn 360° or more.

18. The medical X-ray CT imaging apparatus according to claim 1, further comprising a magnification changing mechanism causing said X-ray detector to be relatively close to or apart from said X-ray source, to thereby change a magnification.

19. The medical X-ray CT imaging apparatus according to claim 1, wherein
 the cylindrical body is in a rotatable state with respect to the support part so as to be rotatable about the rotation axis with respect to the rotation support part, and
 bearings are provided between the rotation support part and the cylindrical body.

20. The medical X-ray CT imaging apparatus according to claim 1, wherein
 the cylindrical body is fixed to the base, and
 bearings are provided between the rotation support part and a support shaft part.

21. The medical X-ray CT imaging apparatus according to claim 1, wherein
 the cylindrical body is in a rotatable state with respect to the support part so as to be rotatable about the rotation axis with respect to the rotation support part, and
 an opening side bearing part and a bottom side bearing part are provided between the rotation support part and the cylindrical body.

22. The medical X-ray CT imaging apparatus according to claim 1, wherein
 the cylindrical body is fixed to the base,
 bearings are provided between the cylindrical body and the base, and
 the cylindrical body is mounted onto the base at a fixed position so as to rotate with respect to the base.

* * * * *